(12) United States Patent
Adnani et al.

(10) Patent No.: US 11,787,763 B2
(45) Date of Patent: Oct. 17, 2023

(54) STRIGOLACTONE DERIVAUVES

(71) Applicant: Plant Response, Inc., Durham, NC (US)

(72) Inventors: Navid Adnani, Emeryville, CA (US); Jonathan Evans, Walnut Creek, CA (US); Hans Holtan, Emeryville, CA (US)

(73) Assignee: Plant Response, Inc., Durham, NC (US)

( * ) Notice: Subject to any disclaimer, the term of this patent is extended or adjusted under 35 U.S.C. 154(b) by 339 days.

(21) Appl. No.: 16/764,444

(22) PCT Filed: Nov. 16, 2018

(86) PCT No.: PCT/IB2018/059073
§ 371 (c)(1),
(2) Date: May 15, 2020

(87) PCT Pub. No.: WO2019/097487
PCT Pub. Date: May 23, 2019

(65) Prior Publication Data
US 2020/0354316 A1    Nov. 12, 2020

Related U.S. Application Data

(60) Provisional application No. 62/587,503, filed on Nov. 17, 2017.

(51) Int. Cl.
| C07D 207/36 | (2006.01) |
| C07D 307/46 | (2006.01) |
| C07D 407/12 | (2006.01) |

(52) U.S. Cl.
CPC ......... *C07D 207/36* (2013.01); *C07D 307/46* (2013.01); *C07D 407/12* (2013.01)

(58) Field of Classification Search
CPC .................................................. C07D 407/12
See application file for complete search history.

(56) References Cited

U.S. PATENT DOCUMENTS

| 8,980,795 | B2* | 3/2015 | Al-Babili | ............. | C07D 307/58 |
| | | | | | 504/299 |
| 9,532,569 | B2* | 1/2017 | Boyer | .................. | C07D 307/68 |
| 10,918,106 | B2 | 2/2021 | Bayer et al. | | |
| 2015/0141255 | A1 | 5/2015 | Boyer et al. | | |

FOREIGN PATENT DOCUMENTS

| EP | 2623502 A1 | 8/2013 |
| JP | WO2010-137662 | * 12/2010 |
| WO | WO 2010/128112 | * 11/2010 |
| WO | 2010137662 A1 | 12/2010 |
| WO | 2015061764 A1 | 4/2015 |
| WO | 2016172655 A1 | 10/2016 |
| WO | 2017025427 A1 | 2/2017 |

OTHER PUBLICATIONS

Boyer et al. (Molecular Plant, 7 (4): 675-690 (2014)).*
WO 2010/137662—Google Patents English translation Jul. 5, 2022.*
Umehara (Plant Cell Physiol. 56(6); 1059-1072 (2015).*
Mwakaboko (Eur. J. Org. Chem. 2016, 3495-3499).*
Ahmadi et al. "Effects of abscisic acid (ABA) on grain filling processes in wheat" Plant Growth Regulation, 28 (3):187-197 (1999).
Astacio et al. "Determining the Effects of Abscisic Acid Drenches on Evapotranspiration and Leaf Gas Exchange of Tomato" Hortscience, 46(11):1512-1517 (2011).
Azizian et al. "Maize response to water, salinity and nitrogen levels: yield-water relation, water-use efficiency and water uptake reduction function" International Journal of Plant Production, 8(2):183-214 (2014).
Bates et al. "Fitting Linear Mixed-Effects Models Using lme4" Journal of Statistical Software, 67(1):1-48 (2015).
Bennett et al. "Strigolactone regulates shoot development through a core signalling pathway" Biology Open, 5 (12):1806-1820 (2016).
Boyer et al. "New Strigolactone Analogs as Plant Hormones with Low Activities in the Rhizosphere" Molecular Plant, 7(4):675-690 (2014).
Condon et al. "Breeding for high water-use efficiency" Journal of Experimental Botany, 55(407):2447-2460 (2004).
Cook et al. "Germination stimulants. II. Structure of strigol, a potent seed germination stimulant for witchweed (*Striga lutea*)" Journal of the American Chemical Society, 94:6198-6199 (1972).
De Dios et al. "Processes driving nocturnal transpiration and implications for estimating land evapotranspiration" Scientific Reports, 5(10975):1-8 (2015).
Díaz-Ambrona et al. "Achieving Global Food Security through Sustainable Development of Agriculture and Food Systems with Regard to Nutrients, Soil, Land, and Waste Management" Current Sustainable/Renewable Energy Reports, 1(2):57-65 (2014).
Du et al. "Exogenous abscisic acid reduces water loss and improves antioxidant defence, desiccation tolerance and transpiration efficiency in two spring wheat cultivars subjected to a soil water deficit" Functional Plant Biology, 40 (5):494-506 (2013).
Fernando et al. "Role of ABA in *Arabidopsis* Salt, Drought, and Desiccation Tolerance" Abiotic and Biotic Stress in Plants—Recent Advances and Future Perspectives, Publisher: Intech, Chapter 22, pp. 507-518 (2016).
Flematti et al. "Stereospecificity in strigolactone biosynthesis and perception" Planta, 243(6):1361-1373 (2016).
Fukui et al. "New branching inhibitors and their potential as strigolactone mimics in rice" Bioorganic & Medicinal Chemistry Letters, 21(16):4905-4908 (2011).
Gong et al. "Genes involved in the synthesis and signaling pathway of strigolactone, a shoot branching inhibitor" Biologia Plantarum, 56(2):210-214 (2012).
Goossens et al. "Elucidating the Structural Isomerism of Fluorescent Strigolactone Analogue CISA-1" European Journal of Organic Chemistry, 2015(6):1211-1217 (2015).

(Continued)

*Primary Examiner* — Valerie Rodriguez-Garcia
(74) *Attorney, Agent, or Firm* — Myers Bigel, P.A.

(57) ABSTRACT

The present disclosure relates to derivatives of strigolactone and formulations thereof. The present disclosure also relates to methods of treating a plant to improve, for example, the yield, growth, or vigor of a plant. The disclosed strigolactone derivatives and formulations may be combined with a plant growth regulator, a fertilizer, an insecticide, an herbicide, a fungicide, a urease inhibitor, a nitrification inhibitor, and/or an excipient.

18 Claims, 9 Drawing Sheets

(56) References Cited

OTHER PUBLICATIONS

Ha et al. "Positive regulatory role of strigolactone in plant responses to drought and salt stress" Proceedings of the National Academy of Sciences USA, 111(2):851-856 (2014).
Haling et al. "Root hairs improve root penetration, root-soil contact, and phosphorus acquisition in soils of different strength" Journal of Experimental Botany, 64(12):3711-3721 (2013).
International Search Report and the Written Opinion of the International Searching Authority corresponding to International Patent Application No. PCT/IB2018/059073 (8 pages) (dated Apr. 29, 2019).
Kijne, Jacob W. "Abiotic stress and water scarcity: Identifying and resolving conflicts from plant level to global level" Field Crops Research, 97(1):3-18 (2006).
Kuromori et al. "ABA Transport and Plant Water Stress Responses" Trends in Plant Science, 23(6):513-522 (2018).
Lumba et al. "Chemical genetics and strigolactone perception" F1000Research, 6(975):1-12 (2017).
Lv et al. "Strigolactone-triggered stomatal closure requires hydrogen peroxide synthesis and nitric oxide production in an abscisic acid-independent manner" New Phytologist, 217(1):290-304 (2018).
Matthys et al. "The Whats, the Wheres and the Hows of strigolactone action in the roots" Planta, 243(6):1327-1337 (2016).
Mori et al. "Carlactone-type strigolactones and their synthetic analogues as inducers of hyphal branching in arbuscular mycorrhizal fungi" Phytochemistry, 130:90-98 (2016).
Mwakaboko "Synthesis and Biological Evaluation of New Strigolactone Analogues as Germination Stimulants for the Seeds of the Parasitic Weeds Striga and Orobanche Spp" retrieved from CAPLUS; STN Database accession No. 2012-1448581 (Jan. 1, 2003).
Mwakaboko et al. "Strigolactone Analogs with a D-Ring Modified at C-2" European Journal of Organic Chemistry, 2016:3495-3499 (2016).
Novák et al. "Transpiration and nutrient uptake dynamics in maize (*Zea mays* L.)" Ecological Modelling, 166:99-107 (2003).
Reid et al. "Mechanisms and control of nutrient uptake in plants" International Review of Cytology—a Survey of Cell Biology, 229:73-114 (2003).
Ruggiero et al. "Uncoupling the Effects of Abscisic Acid on Plant Growth and Water Relations. Analysis of sto1/nced3, an Abscisic Acid-Deficient but Salt Stress-Tolerant Mutant in *Arabidopsis*" Plant Physiology, 136(2):3134-3147 (2004).
Sorefan et al. "MAX4 and RMS1 are orthologous dioxygenase-like genes that regulate shoot branching in *Arabidopsis* and pea" Genes & Development, 17(12):1469-1474 (2003).
Umehara et al. "Structural Requirements of Strigolactones for Shoot Branching Inhibition in Rice and *Arabidopsis*" Plant & Cell Physiology, 56(6):1059-1072 (2015).
Wang et al. "Strigolactone Signaling in *Arabidopsis* Regulates Shoot Development by Targeting D53-Like SMXL Repressor Proteins for Ubiquitination and Degradation" The Plant Cell, 27(11):3128-3142 (2015).
Wang et al. "Vigorous Root Growth Is a Better Indicator of Early Nutrient Uptake than Root Hair Traits in Spring Wheat Grown under Low Fertility" Frontiers in Plant Science, 7(865):1-9 (2016).
Waters et al. "Strigolactone Signaling and Evolution" Annual Review of Plant Biology, 68:291-322 (2017).
Xu et al. "Plant Nitrogen Assimilation and Use Efficiency" Annual Review of Plant Biology, 63(1):153-182 (2012).
Zhaopei et al. "The relation between water use efficiency and photosynthesis characteristic under different N level" Guizhou Agricultural Sciences, 3:27-29 (2009) (English translation of abstract).
Zipper et al. "Drought effects on US maize and soybean production: spatiotemporal patterns and historical changes" Environmental Research Letters, 11:1-11 (2016).

\* cited by examiner

STRIGOLACTONE DERIVATIVES

TECHNICAL FIELD

The present disclosure relates to derivatives of strigolactone and formulations containing them. The present disclosure also relates to methods of using the compounds and formulations disclosed herein to treat a plant to improve, for example, the yield, growth or vigor of the plant.

BACKGROUND

In the face of increasing global demands for food production—and simultaneously shrinking acreage of arable land in the world—there is a pressing need to enhance the efficiency of agronomic practice to improve crop yield while also protecting the sustainability of farm land (Díaz-Ambrona, C. H., Maletta, E. "Achieving Global Food Security through Sustainable Development of Agriculture and Food Systems with Regard to Nutrients, Soil, Land, and Waste Management," *Current Sustainable/Renewable Energy Reports* (2014) Vol. 1 (2), pp. 57-65). To achieve these enhancements, improvements must be made to specific crop performance metrics such as water-use-efficiency (Condon, A. G, et al. "Breeding for high water-use efficiency," *Journal of Experimental Botany*, Vol. 55 (407), pp. 2447-2460), yield stability under abiotic stress (Kijne J. W., Kijne, J. W., "Abiotic stress and water scarcity: Identifying and resolving conflicts from plant level to global level," *Field Crops Research* (2006) Vol. 97 (1), pp. 3-18), and nutrient use efficiency (Xu, G., Fan, X., & Miller, A. J. "Plant Nitrogen Assimilation and Use Efficiency," *Annual Review of Plant Biology, Vol.* 63 (1), pp. 153-182)).

A key mechanistic component underlying all these crop performance metrics is the plants ability to effectively obtain and utilize the water that is available in the soil. Drought, a direct consequence of insufficient water availability, causes significant yield reductions in rainfed agricultural systems, both globally and within the United States (Zipper, S. C. et al., "Drought effects on US maize and soybean production: spatiotemporal patterns and historical changes," *Environmental Research Letters* (2016), Vol. 11 (9), pp. 1-11). Photosynthesis, growth (Zhaopei Z., et al., "The relation between water use efficiency and photosynthesis characteristic under different N level," *Guizhou Agricultural Sciences* (2009) (3), pp. 27-29) and nutrient uptake (Novák, V, & Vidovič, J, "Transpiration and nutrient uptake dynamics in maize (*Zea mays* L.)," *Ecological Modelling* (2003) 166, pp. 99-107) all depend on the movement of water from the soil to the roots and transport to the shoots. The driving mechanism for this water transport is transpiration (Reid, R. J., Hayes, J. E., "Mechanisms and control of nutrient uptake in plants," *International Review of Cytology-a Survey of Cell Biology* (2003), 229, pp. 73-114) both during the day and during the night where photosynthesis is absent (Dios V. R., et al., "Processes driving nocturnal transpiration and implications for estimating land evapotranspiration," *Scientific Reports* (2015) Vol. 5 (1), pp. 10975-10975). Thus, maximal crop performance can be achieved when the plant effectively balances photosynthesis and growth with resource use efficiency given any environmental constraints such as limited soil water content.

Strigolactones (SLs) are a class of small carotenoid-derived plant hormones that share a conserved tricyclic lactone structure, known as the ABC rings, linked via an enol-ether bridge to an α,β-unsaturated furanone moiety termed the D-ring (Flematti, G. R., et al., "Stereospecificity in strigolactone biosynthesis and perception," *Planta* (2016) Vol. 243 (6), pp. 1361-1373). Strigolactone biosynthesis occurs in some algae and in a majority of land plants, suggesting that this signaling pathway is evolutionarily ancient (Waters, M. T., et al., *Annual Review of Plant Biology* (2017) 68 pp. 291-322). The α/β hydrolase superfamily protein, DWARF14 (D14), is the only known receptor for strigolactone molecules in *Arabidopsis thaliana*, and a single ortholog of D14 is found in rice and other diverse species. Crystal structure analysis of D14 has shown that the D-ring of strigolactone binds the receptor pocket, resulting in hydrolysis of the ligand and a conformational change of the receptor from open to closed (Lumba, S., et al., "Chemical genetics and strigolactone perception," *F1000Research* (2017) 6 975, pp. 1-12). This binary conformational change of D14 leads to protein interactions that initiate a strigolactone-signaling cascade.

Application of a range of natural strigolactones and synthetic analogs activate characteristic strigolactone responses in a broad range of plant species. This response reflects the native role that strigolactones play in the regulation of shoot (Bennett, T., et al., "Strigolactone regulates shoot development through a core signalling pathway," *Biology Open* (2016), Vol; 5(12), pp. 1806-1820) and root architecture (Matthys, C., et al., "The Whats, the Wheres and the Hows of strigolactone action in the roots," *Planta*, (2016) Vol. 243 (6), pp. 1327-1337), leaf physiology (Lv, S., et al., "Strigolactone-triggered stomatal closure requires hydrogen peroxide synthesis and nitric oxide production in an abscisic acid-independent manner," *New Phytologist* (2018) Vol. 217 (1), pp. 290-304), abiotic stress response (HaC. V., et al., "Positive regulatory role of strigolactone in plant responses to drought and salt stress," *Proceedings of the National Academy of Sciences of the United States of America* (2014), Vol. 111 (2), pp. 851-856), and the recruitment of symbiotic arbuscular mycorrhizal (AM) fungus (Mori, N., et al., "Carlactone-type strigolactones and their synthetic analogues as inducers of hyphal branching in arbuscular mycorrhizal fungi," *Phytochemistry* (2016) 130, pp. 90-98).

The basic chemical structure of natural strigolactones is represented by Formula 1:

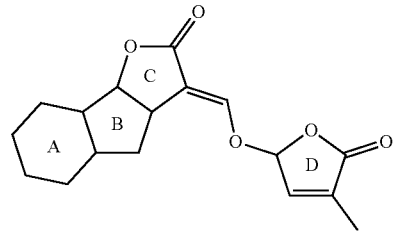

Formula 1

A number of related strigolactones have been identified from different crop root exudates, including for example strigol, sorgolactone, alectrol, and orobanchol (Cook et al., "Germination stimulants. II. Structure of strigol, a potent seed germination stimulant for witchweed (*Striga lutea*)," *J. Am. Chem. Soc.* (1972) Vol. 94, pp. 6198-6199). These molecules, and natural strigolactones generally, are typically tetracyclic compounds with A, B, C, and D rings. The A and B rings may include double bonds and/or substituents.

Natural strigolactones demonstrate a range of beneficial effects, but their limited availability from plant tissues makes them difficult to extract and develop for large-scale applications. The present disclosure solves this problem by providing synthetic strigolactone derivatives, and formulations containing them, as well as methods of treating plants with them. The compounds and formulations in the present disclosure may provide a synergistic effect, ultimately reducing the amount of chemical substances spread into the environment and providing an overall cost savings.

Without being bound by any scientific theory, it is believed that the compounds of the present disclosure activate the strigolactone cascade, by binding to a strigolactone receptor, which in turn induces a conformational change in the receptor that activates the receptor or enables it to interact with binding partners. This interaction then triggers a cascade of reactions in signal transduction which lead to, for example, the biosynthesis of germination promoting products in parasitic plants, the branching factor for arbuscular mycorrhizal fungi, the regulation of plant shoot and root architecture, the regulation of root hair growth, the inhibition of bud outgrowth and of shoot branching, the response to environmental factors, the regulation of leaf physiology, and the response to abiotic stress. The activation of the strigolactone response pathway is also believed to elicit hydraulic enhancement of a plant, which may be demonstrated by increased transpiration of a plant, increased leaf water potential, or a lower plant canopy temperature.

DESCRIPTION OF THE FIGURES

In order to provide an understanding of embodiments of the disclosure, reference is made to the appended figures. These figures are exemplary only, and should not be construed as limiting the disclosure.

DETAILED DESCRIPTION OF THE DISCLOSURE

Figure 1:
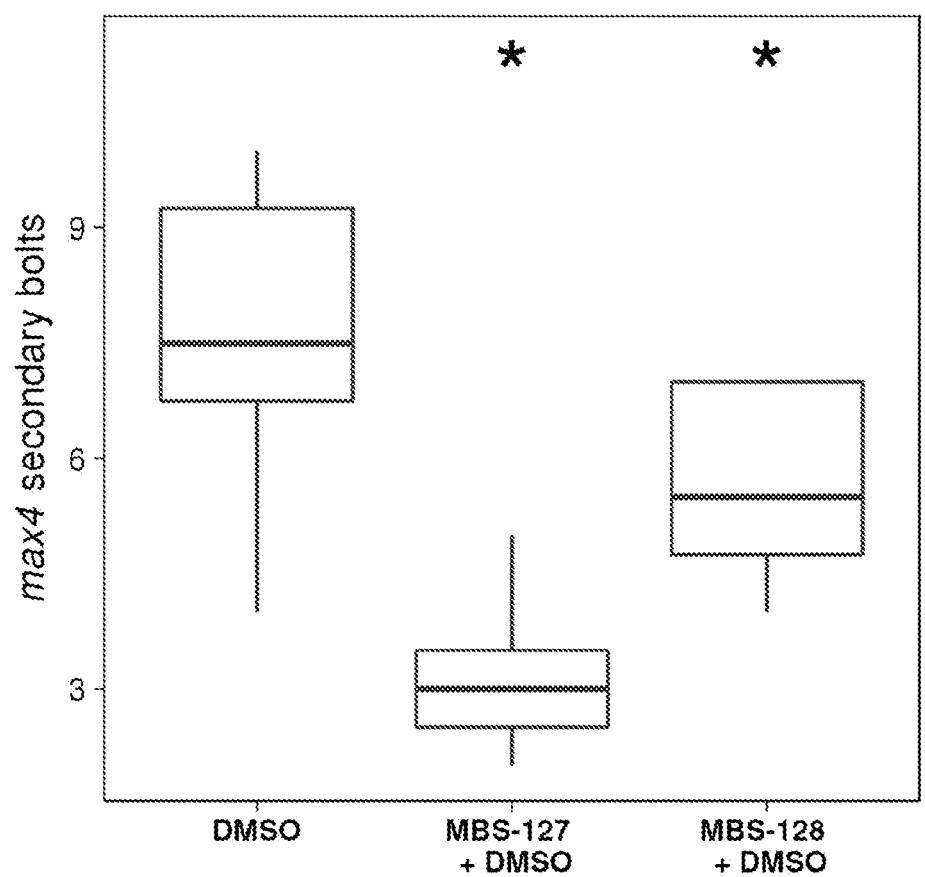
FIG. 1 is a plot of the number of secondary bolts over 0.5 cm long of strigolactone biosynthesis mutant, homozygous max4 knockout, plants that have a primary bolt over 6 cm long treated with solution containing control solvent DMSO, strigolactone molecule MBS-127 in DMSO, and strigolactone molecule MBS-128 in DMSO. Stars indicate significant differences relative to the DMSO control based on the Welch's t-test (*: adjusted p-value<0.1; p-values adjusted for multiple-hypothesis testing FIG. 2 is a boxplot representing $C_t$ value distributions of BRC1 relative to constitutive control $C_t$ values plotted as $\Delta C_t$. Due to the non-normal distribution of the BRC1 data, non-parametric Mann-Whitney U-tests were used to assess statistical significance. Stars indicate significant differences relative to the DMSO control (**: adjusted p-value<0.001; *: adjusted p-value<0.01; p-values adjusted for multiple-hypothesis testing with the Bonferroni correction). Due to the non-normal distribution of the BRC1 data, non-parametric Mann-Whitney U-tests were used to assess statistical significance.

The present disclosure provides a compound of Formula (I):

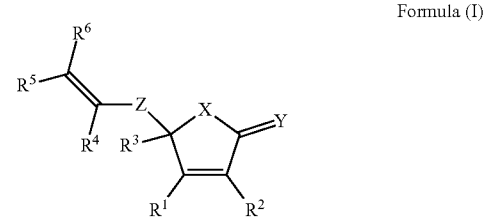

Formula (I)

wherein
X, Y, and Z are independently O, S, or —NR$^7$;
R$^1$, R$^2$, R$^3$, R$^4$, R$^5$, and R$^6$ are each independently H, amino, halo, substituted or unsubstituted alkyl, substituted or unsubstituted aryl, substituted or unsubstituted heteroalkyl, substituted or unsubstituted heteroaryl, substituted or unsubstituted arylalkyl, substituted or unsubstituted cycloalkyl, substituted or unsubstituted heterocycloalkyl, —OR$^8$, —SR$^8$, —C(O)R$^8$, —C(O)OR$^8$, —C(S)R$^8$, —C(S)OR$^8$, —C(S)SR$^8$, —C(O)NRs; or R$^4$ and R$^5$ together with the carbons to which they are attached form a cycloalkyl, cycloalkenyl, heterocycloalkyl, or heterocycloalkenyl ring, which is optionally substituted with one or more substituents selected from amino, halo, alkyl, cycloalkyl, aryl, and oxo; and R$^7$ and R$^8$ are each independently H, substituted or unsubstituted alkyl, substituted or unsubstituted aryl, substituted or unsubstituted heteroalkyl, substituted or unsubstituted heteroaryl, substituted or unsubstituted arylalkyl, substituted or unsubstituted cycloalkyl, or substituted or unsubstituted heterocycloalkyl;

or a salt or solvate thereof.

In at least one embodiment, X, Y, and Z are O. In at least one embodiment, Y and Z are O, and X is —NR$^7$.

In at least one embodiment, R$^1$, R$^2$, R$^3$, R$^4$, and R$^5$ are independently H, substituted or unsubstituted alkyl, or substituted or unsubstituted aryl; and R$^6$ is —OR$^8$, —SR$^8$, —C(O)R$^8$, —C(O)OR$^8$, —C(S)R$^8$, —C(S)OR$^8$, —C(S)SR$^8$, —C(O)NR$^8$.

In at least one embodiment, R$^1$, R$^2$, R$^3$, R$^4$, and R$^5$ are independently a substituted or unsubstituted alkyl. For example, in at least one embodiment, R$^1$ is methyl. In another embodiment, R$^2$ is methyl. In yet another embodiment, R$^3$ is methyl. In at least one other embodiment, R$^1$, R$^2$, and R$^3$ are all methyl.

In at least one embodiment, R$^4$ and R$^5$ together with the carbons to which they are attached form a cycloalkyl, cycloalkenyl, heterocycloalkyl, or heterocycloalkenyl ring, which is optionally substituted with one or more substituents selected from amino, halo, alkyl, cycloalkyl, aryl, and oxo.

In at least one embodiment, R$^7$ and R$^8$ are each independently H, substituted or unsubstituted alkyl, substituted or unsubstituted aryl, substituted or unsubstituted heteroalkyl, substituted or unsubstituted heteroaryl, substituted or unsubstituted arylalkyl, substituted or unsubstituted cycloalkyl, or substituted or unsubstituted heterocycloalkyl.

In at least one embodiment, the compound of Formula I has a structure of Formula (A):

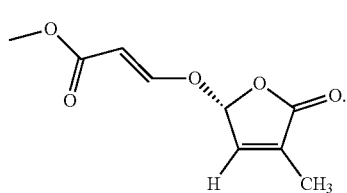

Formula (A)

In at least one embodiment, the compound of Formula I has a structure of Formula (B):

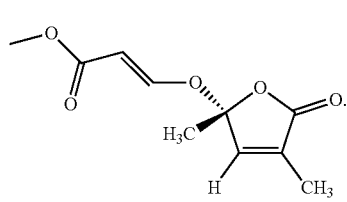

Formula (B)

In at least one embodiment, the compound of Formula I has a structure of Formula (C):

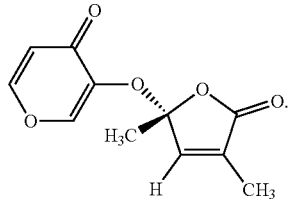

Formula (C)

In at least one embodiment, the compound of Formula I has a structure of Formula (D):

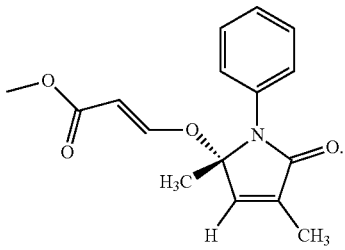

Formula (D)

In at least one embodiment, the compound of Formula I has a structure of Formula (E):

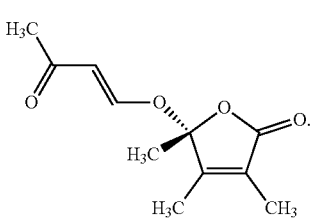

Formula (E)

In at least one embodiment, the compound of Formula I has a structure of Formula (F):

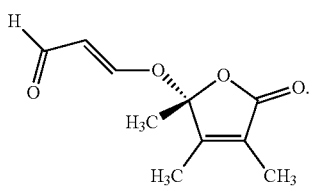

Formula (F)

The present disclosure also provides a compound of Formula (II):

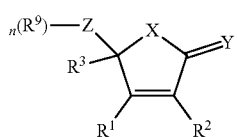

Formula (II)

wherein
X and Y are independently O, S, or —NR⁷;
Z is O, S, —NH, or A;
R¹, R², and R³ are each independently H, amino, halo, substituted or unsubstituted alkyl, substituted or unsubstituted aryl, substituted or unsubstituted heteroalkyl, substituted or unsubstituted heteroaryl, substituted or unsubstituted arylalkyl, substituted or unsubstituted cycloalkyl, substituted or unsubstituted heterocycloalkyl, —OR⁸, —SR⁸, —C(O)R⁸, —C(O)OR⁸, —C(S)R⁸, —C(S)OR⁸, —C(S)SR⁸, —C(O)NR⁸;
R⁷ and R⁸ are each independently H, substituted or unsubstituted alkyl, substituted or unsubstituted aryl, substituted or unsubstituted heteroalkyl, substituted or unsubstituted heteroaryl, substituted or unsubstituted arylalkyl, substituted or unsubstituted cycloalkyl, or substituted or unsubstituted heterocycloalkyl;
A is a substituted or unsubstituted heterocyclic group or substituted or unsubstituted heteroaryl group;
R⁹ is H, substituted or unsubstituted alkyl, substituted or unsubstituted aryl, substituted or unsubstituted heteroalkyl, substituted or unsubstituted heteroaryl, substituted or unsubstituted arylalkyl, substituted or unsubstituted cycloalkyl, substituted or unsubstituted heterocycloalkyl, —C(O)R⁸, —C(O)OR⁸, —C(S)R⁸, —C(S)OR⁸, —C(S)SR⁸, or —C(O)NR⁸; and
n is 1, 2 or 3;
or a salt or solvate thereof.

The term "substituent" denotes an atom or a group of atoms replacing a hydrogen atom on the parent molecule. The term "substituted" denotes that a specified group bears one or more substituents. Where any group may carry multiple substituents, a variety of possible substituents is provided. The substituents are independently selected and need not to be the same. The term "unsubstituted" means that the specified group bears no substituents. The term "optionally substituted" means that the specified group is unsubstituted or substituted by one or more substituents, independently chosen from the group of possible substituents. When indicating the number of substituents, the term "one or more" refers to a range from one substituent to the highest possible number of substituents, i.e. replacement of from one hydrogen up to replacement of all hydrogen atoms by substituents.

The compound, salt, or solvate of the present disclosure may be an isomer. Isomers include, for example, constitutional or structural isomers, stereoisomers (enantiomers and diastereomers), geometric isomers, tautomers, confomers, and rotamers. In at least one embodiment, the isomer of the compound, salt, or solvate of the present disclosure is a stereoisomer. In at least one embodiment, the stereoisomer of the compound, salt, or solvate of the present disclosure is an enantiomer. When the stereoisomer is an enantiomer, it may have an enantiomeric excess of at least about 50%, 60%, 70%, 80%, 85%, 90%, or 95%, or from at least about 50% to 100%. The stereoisomer may have an enantiomeric excess of at least about 15%, 20%, 30%, 40%, 50%, 60%, 70%, 80%, 85%, 90%, 95%, or 99%. The stereoisomer may have an enantiomeric excess of about 15%-99%, 20%-99%, 30%-99%, 40-99%, 50-99%, 60-99%, 70-99%, 80-99%, 90-99%, 15%-90%, 20%-90%, 30%-90%, 40-90%, 50-90%, 60-90%, 70-90%, 80-90%, 15%-80%, 20%-80%, 30%-80%, 40-80%, 50-80%, 60-80%, 70-80%, 15%-70%, 20%-70%, 30%-70%, 40-70%, 50-70%, 60-70%, 15%-60%, 20%-60%, 30%-60%, 40-60%, 50-60%, 15%-50%, 20%-50%, 30%-50%, 40-50%, 15%-40%, 20%-40%, 30%-40%, 15%-30%, 20%-30%, or 15-20%. In at least one embodiment, the stereoisomer may have an enantiomeric excess of from at least about 50% to 100%.

The stereoisomer of the compound, salt, or solvate of the present disclosure may alternatively be a diastereoisomer. In at least one embodiment, the stereoisomer is a diastereoisomer having a diastereomeric excess of at least about 50%, 60%, 70%, 80%, 85%, 90%, or 95%, or from at least about 50% to 100%. The stereoisomer may have a diastereomeric excess of at least about 15%, 20%, 30%, 40%, 50%, 60%, 70%, 80%, 85%, 90%, 95%, or 99%. The stereoisomer may have a diastereomeric excess of about 15%-99%, 20%-99%, 30%-99%, 40-99%, 50-99%, 60-99%, 70-99%, 80-99%, 90-99%, 15%-90%, 20%-90%, 30%-90%, 40-90%, 50-90%, 60-90%, 70-90%, 80-90%, 15%-80%, 20%-80%, 30%-80%, 40-80%, 50-80%, 60-80%, 70-80%, 15%-70%, 20%-70%, 30%-70%, 40-70%, 50-70%, 60-70%, 15%-60%, 20%-60%, 30%-60%, 40-60%, 50-60%, 15%-50%, 20%-50%, 30%-50%, 40-50%, 15%-40%, 20%-40%, 30%-40%, 15%-30%, 20%-30%, or 15-20%. In at least one embodiment, the stereoisomer may have a diastereomeric excess of from at least about 50% to 100%.

The isomer of the compound, salt, or solvate of the present disclosure may be a geometric isomer of the compound, salt, or solvate of the present disclosure. In at least one embodiment, the geometric isomer is an E-isomer. In another embodiment, the geometric isomer is a Z-isomer isomer.

The present disclosure also includes a formulation comprising (i) a compound of Formula (I):

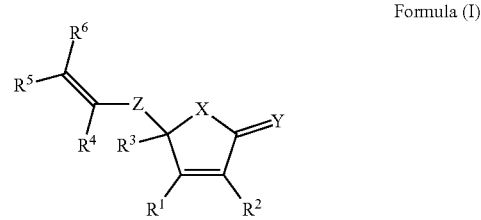

Formula (I)

wherein
X, Y, and Z are independently O, S, or —NR⁷;
R¹, R², R³, R⁴, R⁵, and R⁶ are each independently H, amino, halo, substituted or unsubstituted alkyl, substituted or unsubstituted aryl, substituted or unsubstituted heteroalkyl, substituted or unsubstituted heteroaryl, substituted or unsubstituted arylalkyl, substituted or unsubstituted cycloalkyl, substituted or unsubstituted heterocycloalkyl, —OR⁸, —SR⁸, —C(O)R⁸, —C(O)OR⁸, —C(S)R⁸, —C(S)OR⁸, —C(S)SR⁸, —C(O)NR⁸; or R⁴ and R⁵ together with the carbons to which they are attached form a cycloalkyl, cycloalkenyl, heterocycloalkyl, or heterocycloalkenyl ring, which is optionally substituted with one or more substituents selected from amino, halo, alkyl, cycloalkyl, aryl, and oxo; and
R⁷ and R⁸ are each independently H, substituted or unsubstituted alkyl, substituted or unsubstituted aryl, substituted or unsubstituted heteroalkyl, substituted or unsubstituted heteroaryl, substituted or unsubstituted arylalkyl, substituted or unsubstituted cycloalkyl, or substituted or unsubstituted heterocycloalkyl;
or a salt or solvate thereof; and
(ii) a plant growth regulator, a fertilizer, an insecticide, an herbicide, a fungicide, a urease inhibitor, a nitrification inhibitor, and/or an excipient.

The present disclosure also includes a formulation comprising (i) a compound of Formula II:

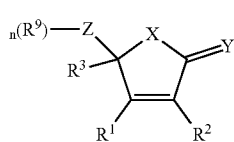

Formula II wherein
X, and Y are independently O, S, or —NR$^7$;
Z is O, S, —NH, or A;
R$^1$, R$^2$, and R$^3$ are each independently H, amino, halo, substituted or unsubstituted alkyl, substituted or unsubstituted aryl, substituted or unsubstituted heteroalkyl, substituted or unsubstituted heteroaryl, substituted or unsubstituted arylalkyl, substituted or unsubstituted cycloalkyl, substituted or unsubstituted heterocycloalkyl, —OR, —SR, —C(O)R$^8$, —C(O)OR$^8$, —C(S)R$^8$, —C(S)OR$^8$, —C(S)SR$^8$, —C(O)NR$^8$;
R$^7$ and R$^8$ are each independently H, substituted or unsubstituted alkyl, substituted or unsubstituted aryl, substituted or unsubstituted heteroalkyl, substituted or unsubstituted heteroaryl, substituted or unsubstituted arylalkyl, substituted or unsubstituted cycloalkyl, or substituted or unsubstituted heterocycloalkyl;
A is a substituted or unsubstituted heterocyclic group or substituted or unsubstituted heteroaryl group;
R$^9$ is H, substituted or unsubstituted alkyl, substituted or unsubstituted aryl, substituted or unsubstituted heteroalkyl, substituted or unsubstituted heteroaryl, substituted or unsubstituted arylalkyl, substituted or unsubstituted cycloalkyl, substituted or unsubstituted heterocycloalkyl, —C(O)R$^8$, —C(O)OR$^8$, —C(S)R$^8$, —C(S)OR$^8$, —C(S)SR$^8$, or —C(O)NR$^8$; and
n is 1, 2 or 3;
or a salt or solvate thereof; and
(ii) a plant growth regulator, a fertilizer, an insecticide, an herbicide, a fungicide, a urease inhibitor, a nitrification inhibitor, and/or an excipient.

The compound of Formula (I) or Formula (II), plant growth regulator, fertilizer, insecticide, herbicide, fungicide, urease inhibitor, nitrification inhibitor and/or excipient may be present in a formulation of the present disclosure each individually or collectively in an amount of at least about 1 mg, 5 mg, 10 mg, 20 mg, 30 mg, 40 mg, 50 mg, 100 mg, 200 mg, 300 mg, 400 mg, 500 mg, 1 g, 5 g, 10 g, 50 g, 100 g, 500 g, 1 kg, 5 kg, 10 kg, 50 kg, 100 kg, or 1000 kg.

The compound of Formula (I) or Formula (II), plant growth regulator, fertilizer, insecticide, herbicide, fungicide, urease inhibitor, nitrification inhibitor and/or an excipient may be present in a formulation of the present disclosure each individually or collectively in an amount from about 1 mg to about 1000 kg. In at least one embodiment, the amount is in the range of 1 mg to 10 mg. In another embodiment, the amount is in the range of 10 mg to 50 mg, 50 mg to 100 mg, 100 mg to 500 mg, or 500 mg to 1 g. In another embodiment, the amount is in the range of 1 g to 10 g, 10 g to 100 g, 100 g to 1 kg, 1 kg to 10 kg, 10 kg to 100 kg, or 100 kg to 500 kg.

The compound of Formula (I) or Formula (II) may be present in an amount of at least about 1%, 5%, 10%, 20%, 30%, 40%, 50%, 60%, 70%, 80%, 90%, 95%, or 99% by weight of the total weight of the formulation. In at least one embodiment, the compound of Formula (I) or Formula (II) is present in an amount ranging from about 1% to 99% by weight of the total weight of the formulation, such as from 1-5%, 1-10%, 1-15%, 1-20%, 1-30%, 1-40%, or 1-50%. In another embodiment, the compound of Formula I or Formula II is present in an amount ranging from about 10% to 99% by weight of the total weight of the formulation, such as from 10-20%, 10-30%, 10-40%, 10-50%, 10-75%, or 10-95% by weight of the total weight of the formulation.

A formulation of the present disclosure may also include a urease inhibitor. As used herein, "urease inhibitor" refers to any compound that reduces, inhibits, or otherwise slows down the conversion of urea to ammonium (NH$_4^+$) in soil when present as compared to the conversion of urea to ammonium (NH$_4^+$) in soil when not present. Examples of urease inhibitors include, but are not limited to, N-(n-butyl) thiophosphoric triamide (NBPT), N-(n-butyl)thiophosphorictriamide, N-(n-butyl)phosphoric triamide, thiophosphoryl triamide, phenylphosphorodiamidate, cyclohexyl phosphoric triamide, cyclohexyl thiophosphoric triamide, phosphoric triamide, hydroquinone, p-benzoquinone, hexamidocyclotriphosphazene, thiopyridines, thiopyrimidines, thiopyridine-N-oxides, N,N-dihalo-2-imidazolidinone, N-halo-2-oxazolidinone and derivatives thereof. In at least one embodiment, the urease inhibitor such as for example, NBPT, is present in the formulation of the present disclosure, in an amount of from about 1% to 99% by weight of the total weight of the formulation. The urease inhibitor may be present in the formulation of the present disclosure in an amount ranging from about 1% to 70% by weight, such as from 1% to 60% by weight, such as from 1% to 50%, such as from 1% to 40%, such as from 1% to 30%, such as from 1% to 20%, such as from 1% to 10%, such as from 1% to 5%. The urease inhibitor may be present in the formulation of the present disclosure in a range of about 5% to 60%, such as 5% to 50%, 5% to 40%, or 5% to 30%. The urease inhibitor may be present in the formulation of the present disclosure in a range of about 10% to 60%, such as 10% to 50%, 10% to 40%, or 10% to 30%. The urease inhibitor may be present in the formulation of the present disclosure in a range of about 15% to 60%, such as 15% to 50%, 15% to 40%, or 15% to 30%. The urease inhibitor may be present in the formulation of the present disclosure in a range of about 30% to 60%, such as 30% to 50%, such as 40% to 60%.

A formulation of the present disclosure may include a nitrification inhibitor. As used herein, "nitrification inhibitor" refers to any compound that reduces, inhibitors, or otherwise slows down the conversion of ammonium (NH$_4$) to nitrate in soil when present as compared to the conversion of ammonium (NH$_4$) to nitrate in soil when not present. Examples of nitrification inhibitors include, but are not limited to, dicyandiamide (DCD), 2-chloro-6-trichloromethyl-pyridine, 5-ethoxy-3-trichloromethyl-1,2,4-thiadiazole, dicyandiamide, 2-amino-4-chloro-6-methyl-pyrimidine, 1,3-benzothiazole-2-thiol, 4-amino-N-1,3-thiazol-2-ylbenzenesulfonamide, thiourea, guanidine, 3,4-dimethylpyrazole phosphate, 2,4-diamino-6-trichloromethyl-5-triazine, polyetherionophores, 4-amino-1,2,4-triazole, 3-mercapto-1, 2,4-triazole, potassium azide, carbon bisulfide, sodium trithiocarbonate, ammonium dithiocarbamate, 2,3-dihydro-2, 2-dimethyl-7-benzofuranol methyl-carbamate, N-(2,6-dimethylphenyl)-N-(methoxyacetyl)-alanine methyl ester, ammonium thiosulfate, 1-hydroxypyrazole, 2-methylpyrazole-1-carboxamide, derivatives thereof, and any combination thereof. In at least one embodiment, the nitrification inhibitor such as for example DCD, is present in the formulation of the present disclosure, in an amount of from about 1% to 99% by weight of the total weight of the formulation. The nitrification inhibitor may be present in the formulation of the present disclosure in an amount ranging from about 1% to 70% by weight, such as from 1% to 60% by weight, such as from 1% to 50%, such as from 1% to 40%, such as from 1% to 30%, such as from 1% to 20%, such as from 1% to 10%, such as from 1% to 5%. The nitrification inhibitor may be present in the formulation of the present disclosure in a range of about 5% to 60%, such as 5% to 50%, 5% to 40%, or 5% to 30%. The nitrification inhibitor may be present in the formulation of the present disclosure in a range of about 10% to 60%, such as 10% to 50%, 10% to 40%, or 10% to 30%. The nitrification inhibitor may be present in the formulation of the present disclosure in a range of about 15% to 60%, such as 15% to 50%, 15% to 40%, or 15% to 30%. The nitrification inhibitor may be present in the formulation of the present disclosure in a range of about 30% to 60%, such as 30% to 50%, such as 40% to 60%.

A formulation of the present disclosure may also include one or more excipients. The excipient may be water, a surfactant, an alcohol, or any combination thereof. In at least one embodiment, the surfactant is selected from sulfosuccinate, naphthalene sulfonate, sulfated ester, phosphate ester, sulfated alcohol, alkyl benzene sulfonate, polycarboxylate, naphthalene sulfonate condensate, phenol sulfonic acid condensate, lignosulfonate, methyl oleyl taurate, polyvinyl alcohol, or any combination thereof.

A formulation of the present disclosure may include a fertilizer. In at least one embodiment, the fertilizer is selected from a nitrogen-containing fertilizer, phosphate-containing fertilizer, potassium-containing fertilizer, calcium-containing fertilizer, magnesium-containing fertilizer, sulfur-containing fertilizer, compound fertilizer, organic fertilizer, or any combination thereof.

A formulation of the present disclosure may include an insecticide, a fungicide, an herbicide, or any combination thereof. In at least one embodiment, the herbicide is a glyphosate. In at least one embodiment, the glyphosate is N-(phosphonomethyl)glycine.

A formulation of the present disclosure may also include additional components, such as xanthan gum; calcium carbonate (agricultural lime) in its various forms for adding weight and/or raising the pH of acidic soils; metal containing compounds and minerals such as for example, gypsum, metal silicates, and chelates of various micronutrient metals such as for example, iron, zinc and manganese; talc; elemental sulfur; activated carbon, which may act as a "safener" to protect against potentially harmful chemicals in the soil; plant protectants; nutrients; nutrient stabilizers; super absorbent polymers; wicking agents; wetting agents; plant stimulants to accelerate growth; inorganic nitrogen, phosphorus, potassium (N—P—K) type fertilizers; sources of phosphorus; sources of potassium; organic fertilizers; surfactants, such as for example, alkylaryl polyether alcohols; initiators; stabilizers; cross linkers; antioxidants; UV stabilizers; reducing agents; dyes, such as for example, blue dye (FD & C blue #1); pesticides; herbicides; fungicides; and plasticizers. The content of these optional additional components of the present disclosure can be present in an amount ranging from about 1% to about 75% by weight of the total weight of the formulation and depends, in part, on the desired function of the additional components and the makeup of the formulation to which the additional components are added. Examples of conditioners include, but are not limited to, tricalcium phosphate, sodium bicarbonate, sodium ferricyanide, potassium ferricyanide, bone phosphate, sodium silicate, silicon dioxide, calcium silicate, talcum powder, bentonite, calcium aluminum silicate, stearic acid, and polyacrylate powder. Examples of plant protectants and nutrient stabilizers include silicon dioxide and the like. Examples of nutrients include, but are not limited to, phosphorus and potassium based nutrients. A commercially available fertilizer nutrient can include, for example, K-Fol 0-40-53, which is a solution that contains 40 wt. % phosphate and 53 wt. % potassium, which is manufactured and distributed by GBS Biosciences, LLC.

A formulation of the present disclosure may be in the form of a powder formulation, a solid formulation, a gel, or a liquid formulation. In at least one embodiment, the formulation is a powder formulation. In at least one embodiment, the formulation is a solid formulation. In at least one embodiment, the formulation is a liquid formulation.

The present disclosure also includes a solid carrier-based formulation, wherein the solid carrier is selected from mineral earths, such as for example, silicates, silica gels, talc, kaolins, limestone, lime, chalk, clays, dolomite, diatomaceous earth, bentonite, montmorillonites; inorganic salts, such as for example, aluminum sulfate, calcium sulfate, copper sulfate, iron sulfate, magnesium sulfate, silicon sulfate, magnesium oxide; polysaccharides, such as for example, cellulose, starch; fertilizers, such as for example, ammonium sulfate, ammonium phosphate, ammonium nitrate; products of vegetable origin, such as for example, cereal meal, tree bark meal, wood meal, nutshell meal; grain flours suitable for the use in the present disclosure, such as for example, flours from corn, rice, wheat, barley, sorghum, millet, oat, triticale, rye, buckwheat, fonio and quinoa, and mixtures thereof.

The present disclosure also provides a solvent-based formulation, wherein the solvent is selected from alkanolamines, such as for example, triethanolamine, diethanolamine, monoethanolamine; alkyldiethanolamines, dialkylmonoethanolamines, wherein the alkyl group is $C_1$-$C_{24}$ branched or unbranched alkyl chain; dimethylsulfoxide (DMSO); alkylsulfones, such as for example, sulfolane (2,3,4,5-tetrahydrothiophene-1,1-dioxide); alkyl amides, such as for example, N-methylpyrrolidone, N-ethylpyrrolidone, or dimethylformamide; monoalcohols, such as for example, methanol, ethanol, propanol, isopropanol, or benzyl alcohol; glycols, such as for example, ethylene glycol, propylene glycol, diethylene glycol, or dipropylene glycol; glycol derivatives and protected glycols, such as for example, triethylene glycol monobutyl ether; glycerol and glycerol derivatives (trialcohols) including protected glycerols, such as for example, isopropylidine glycerol; dibasic esters and derivatives thereof; alkylene carbonates, such as for example, ethylene carbonate or propylene carbonate; monobasic esters, such as for example, ethyl lactate or ethyl acetate; polymers of carboxylic acids, such as for example, maleic acid, oleic acid, itaconic acid, acrylic acid, or methacrylic acid; monoalkyl glycol ethers and dialkyl glycol ethers; glycol esters; surfactants, such as for example, alkylbenzenesulfonates, lignin sulfonates, alkylphenol ethoxylates, or polyethoxylated amines.

The present disclosure includes methods for treating a plant. As used herein, "plant" can be used interchangeably with "crop" and can include, but is not limited to any crop, cultivated plant, fungus, or alga that is harvested for food, clothing, livestock fodder, biofuel, medicine, or other uses. For example, plants include field and greenhouse crops, including but not limited to broad acre crops, fruits and vegetables, perennial tree crops, and ornamentals. Plants also include, but are not limited, to sugarcane, pumpkin, maize (corn), wheat, rice, cassava, soybeans, hay, potatoes, cotton, tomato, alfalfa, and green algae. Plants also include, but are not limited to, any vegetable, such as for example, cabbage, turnip, carrot, parsnip, beetroot, lettuce, beans, broad beans, peas, potato, eggplant, tomato, cucumber, squash, onion, garlic, leek, pepper, spinach, yam, and sweet potato.

A plant may be treated by contacting it directly with a compound, salt, solvate, or formulation of the present disclosure. In at least one embodiment, contacting a plant comprises indirectly contacting the plant by contacting soil surrounding the plant with a compound, salt, solvate, or formulation of the present disclosure. In another embodiment, contacting the plant with a compound, salt, solvate, or formulation of the present disclosure may comprise administering a compound, salt, solvate, or formulation of the present disclosure as a spray. In another embodiment, contacting a plant comprises administering a compound, salt, solvate, or formulation of the present disclosure as a powder. In at least one embodiment, contacting the plant with a compound, salt, solvate, or formulation of the present disclosure may comprise adding a compound, salt, solvate, or formulation of the present disclosure to the irrigation water of the plant. Alternatively, contacting a plant with a compound, salt, solvate, or formulation of the present disclosure may comprise applying a compound, salt, solvate, or formulation of the present disclosure to the habitat of the plant. In at least one embodiment, contacting a plant with a compound, salt, solvate, or formulation of the present disclosure may comprise adding a compound, salt, solvate, or formulation of the present disclosure to a plant container (e.g., vase) and placing the plant in the plant container. In another embodiment, contacting a plant with a compound, salt, solvate, or formulation of the present disclosure may comprise adding a compound, salt, solvate, or formulation of the present disclosure to soil surrounding the plant.

The present disclosure also provides for a method of eliciting hydraulic enhancement of a plant comprising contacting the plant with a compound, salt, solvate, or formulation of the present disclosure.

The present disclosure also relates to a method for increasing the yield of a plant comprising contacting the plant with a compound, salt, solvate, or formulation of the present disclosure, wherein the yield of the contacted plant is increased as compared to a substantially identical but otherwise uncontacted plant. As used herein, "substantially identical plant" can refer to a plant of the same species as an earlier-referenced plant. For example, a substantially identical but otherwise uncontacted plant belongs to the same species as a contacted plant. The substantially identical but otherwise uncontacted plant can have a height of about 80% to 120% of the contacted plant (as measured from the surrounding soil to the highest point of the plant) and/or can have a mass of about 80% to 120% of the contacted plant. In at least one embodiment, the yield of the contacted plant is increased by at least about 0.1%, at least about 0.2%, at least about 0.3%, at least about 0.4%, at least about 0.5%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% as compared to a substantially identical but otherwise uncontacted plant.

In at least one embodiment, the yield of the contacted plant is increased by about 0.1%-1%, 0.1%-5%, about 0.1-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, about 90%-100%, about 95%-99%, or about 99%-100% as compared to a substantially identical but otherwise uncontacted plant.

The present disclosure also provides for a method for eliciting hydraulic enhancement of a plant comprising contacting the plant with a compound, salt, solvate, or formulation of the present disclosure, wherein, the yield of the contacted plant is increased under an adequately irrigated condition or a drought condition. As used herein, "drought" can mean conditions with less than 20 inches, such as for example, less than 15 inches, less than 10 inches, or less than 5 inches, of rainfall within the past 12 months. The term "drought" can also mean conditions with a Palmer Drought Severity Index (PDSI) of less than −1.0. As used herein, "adequately irrigated condition" can mean a condition with more than 20 inches of rainfall within the past 12 months. The term "adequately irrigated condition" can also mean a condition with a PDSI of more than −1.0.

The present disclosure also provides a method for eliciting hydraulic enhancement of corn comprising contacting the corn plant with a compound, salt, solvate, or formulation of the present disclosure, wherein the yield of the contacted corn is increased as compared to a substantially identical but otherwise uncontacted corn. In at least one embodiment, an average kernel mass (w/w) of the contacted corn is increased by at least about 1%, 5%, 10%, 20%, 30%, 40%, 50%, 60%, 70%, 80%, 90%, 95%, or 99%, or from about 0.1%-1%, about 0.1%-5%, about 0.1-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, about 90%-100%, about 95%-99%, or about 99%-100% as compared to a substantially identical but otherwise uncontacted corn. In at least one embodiment, an average ear volume (v/v) of the contacted corn is increased by at least about 1%, 5%, 10%, 20%, 30%, 40%, 50%, 60%, 70%, 80%, 90%, 95%, or 99%, or from about 0.1%-1%, about 0.1%-5%, about 0.1-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, about 90%-100%, about 95%-99%, or about 99%-100% as compared to a substantially identical but otherwise uncontacted corn.

In at least one embodiment, an average relative hydration of silks (w/w) of the contacted corn is increased by at least about 1%, 5%, 10%, 20%, 30%, 40%, 50%, 60%, 70%, 80%, 90%, 95%, or 99%, or from about 0.1%-1%, about 0.1%-5%, about 0.1-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, about 90%-100%, about 95%-99%, or about 99%-100% as compared to a substantially identical but otherwise uncontacted corn.

In at least one embodiment, an average mass of silks (w/w) of the contacted corn is increased by at least about 1%, 5%, 10%, 20%, 30%, 40%, 50%, 60%, 70%, 80%, 90%, 95%, or 99%, or from about 0.1%-1%, about 0.1%-5%, about 0.1-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, about 90%-100%, about 95%-99%, or about 99%-100% as compared to a substantially identical but otherwise uncontacted corn.

The present disclosure also includes a method for eliciting hydraulic enhancement of a plant comprising contacting the plant with a compound, salt, solvate, or formulation of the present disclosure, wherein transpiration of the contacted plant is increased as compared to a substantially identical but otherwise uncontacted plant.

The transpiration of the plant may be measured as peak stomatal conductance. In at least one embodiment, the transpiration of the plant is measured using a leaf porometer. In at least one embodiment, the transpiration of the contacted plant is increased by at least about 1%, 5%, 10%, 20%, 30%, 40%, 50%, 60%, 70%, 80%, 90%, 95%, or 99% as compared to a substantially identical but otherwise uncontacted plant. In at least one embodiment, the transpiration of the contacted plant is increased by about 0.1%-1%, about 0.1%-5%, about 0.1-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, about 90%-100%, about 95%-99%, or about 99%-100% as compared to a substantially identical but otherwise uncontacted plant.

The transpiration of the plant may also be measured as canopy temperature. In at least one embodiment, the transpiration of the plant is measured by using an infrared camera. In at least one embodiment, the canopy temperature of the contacted plant is decreased by at least about 0.1° C., 0.2° C., 0.3° C., 0.4° C., 0.5° C., 0.6° C., 0.7° C., 0.8° C., 0.9° C., 1° C., 1.5° C., 2° C., 2.5° C., 3° C., 3.5° C., 4° C., 4.5° C., 5° C., 5.5° C., 6° C., 6.5° C., 7° C., 7.5° C., 8° C., 8.5° C., 9° C., 9.5° C., 10° C., 11° C., 12° C., 13° C., 14° C., 15° C., 16° C., 17° C., 18° C., 19° C., 20° C., or 25° C. as compared to a substantially identical but otherwise uncontacted plant. In at least one embodiment, the canopy temperature of the contacted plant is decreased by about 0.1 to about 1.0° C., about 1.0 to about 2.0° C., about 2.0 to about 5.0° C., or about 5.0 to about 10° C. as compared to a substantially identical but otherwise uncontacted plant.

The transpiration of the plant may also be measured as transpired water volume. In at least one embodiment, the transpiration of the plant is measured by using an ex vivo hydraulic enhancement assay (xVHS). In at least one embodiment, the transpiration of the contacted plant is increased by at least about 0.1 mL, 0.2 mL, 0.3 mL, 0.4 mL, 0.5 mL, 0.6 mL, 0.7 mL, 0.8 mL, 0.9 mL, 1 mL, 1.5 mL, 2 mL, 2.5 mL, 3 mL, 3.5 mL, 4 mL, 4.5 mL, 5 mL, 5.5 mL, 6 mL, 6.5 mL, 7 mL, 7.5 mL, 8 mL, 8.5 mL, 9 mL, 9.5 mL, 10 mL, 11 mL, 12 mL, 13 mL, 14 mL, 15 mL, 16 mL, 17 mL, 18 mL, 19 mL, 20 mL, or 25 mL as compared to a substantially identical but otherwise uncontacted plant.

In at least one embodiment, the transpiration of the contacted plant is increased by at least about 0.1 to 0.2 mL, about 0.2 to 0.3 mL, about 0.3 to 0.4 mL, about 0.4 to 0.5 mL, about 0.5 to 0.6 mL, about 0.6 to 0.7 mL, about 0.7 to 0.8 mL, about 0.8 to 0.9 mL, about 0.9 to 1 mL, about 1 to 5 mL, or about 5 to 10 mL, as compared to a substantially identical but otherwise uncontacted plant. In at least one embodiment, the transpiration is increased by at least about 1%, 5%, 10%, 20%, 30%, 40%, 50%, 60%, 70%, 80%, 90%, 95%, or 99% as compared to a substantially identical but otherwise uncontacted plant. In at least one embodiment, the transpiration of the contacted plant is increased by about 0.1%-1%, 0.1%-5%, about 0.1-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, about 90%-100%, about 95%-99%, or about 99%-100% as compared to a substantially identical but otherwise uncontacted plant.

The present disclosure also relates to a method for decreasing the permanent wilting point of a plant comprising contacting the plant with a compound, salt, solvate, or formulation of the present disclosure, wherein the permanent wilting point of the contacted plant is decreased as compared to a substantially identical but otherwise uncontacted plant. In at least one embodiment, the permanent wilting point of the plant is measured as volumetric water content of soil ($m^3/m^3$). In at least one embodiment, the permanent wilting point of the contacted plant is decreased by at least about 0.005 $m^3/m^3$, 0010 $m^3/m^3$, 0.015 $m^3/m^3$, 0.020 $m^3/m^3$, 0.025 $m^3/m^3$, 0.030 $m^3/m^3$, 0.035 $m^3/m^3$, 0.040 $m^3/m^3$, 0.045 $m^3/m^3$, 0.050 $m^3/m^3$, 0.055 $m^3/m^3$, 0.060 $m^3/m^3$, 0.070 $m^3/m^3$, 0.080 $m^3/m^3$, 0.090 $m^3/m^3$, or 0.1 $m^3/m^3$, or from about 0.005 $m^3/m^3$ to about 0.1 $m^3/m^3$, for example about 0.005 $m^3/m^3$ to about 0.01 $m^3/m^3$, about 0.01 $m^3/m^3$ to about 0.02 $m^3/m^3$, about 0.02 $m^3/m^3$ to about 0.03 $m^3/m^3$, about 0.03 $m^3/m^3$ to about 0.04 $m^3/m^3$, about 0.04 $m^3/m^3$ to about 0.05 $m^3/m^3$, about 0.05 $m^3/m^3$ to about 0.06 $m^3/m^3$, about 0.06 $m^3/m^3$ to about 0.07 $m^3/m^3$, about 0.07 $m^3/m^3$ to about 0.08 $m^3/m^3$, about 0.08 $m^3/m^3$ to about 0.09 $m^3/m^3$, or about 0.09 $m^3/m^3$ to about 0.10 $m^3/m^3$, as compared to a substantially identical but otherwise uncontacted plant.

In at least one embodiment, the permanent wilting point of the contacted plant is decreased by at least about 1%, 5%, 10%, 20%, 30%, 40%, 50%, 60%, 70%, 80%, 90%, 95%, or 99% or from about 0.1%-1%, about 0.1%-5%, about 0.1-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, about 90%-100%, about 95%-99%, or about 99%-100% as compared to a substantially identical but otherwise uncontacted plant.

The present disclosure relates to a method for decreasing an average rate of cavitation in xylem of the contacted plant as compared to a substantially identical but otherwise uncontacted plant. The average rate of cavitation in xylem of the plant may be measured using an ultrasonic acoustic emission (UAE). In at least one embodiment, the average rate of cavitation in xylem of the contacted plant is decreased by at least about %, 5%, 10%, 20%, 30%, 40%, 50%, 60%, 70%, 80%, 90%, 95%, or 99%, or from about 0.1%-1%, about 0.1%-5%, about 0.1-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, about 90%-95%, about 90%-99%, about 90%-100%, about 95%-99%, or about 99%-100% as compared to a substantially identical but otherwise uncontacted plant.

The present disclosure relates to methods of enhancing shoot growth, comprising contacting the plant with a compound, salt, solvate, or formulation of the present disclosure, wherein the shoot growth is increased as compared to a substantially identical but otherwise uncontacted plant. Shoot growth may be enhanced by at least about 5%, by at least about 10%, 15%, 20%, 25%, or 50%.

The present disclosure includes methods of improving agriculture comprising applying a formulation comprising a compound, salt, solvate, or formulation of the present disclosure to a plant, thereby improving agriculture. Improving agriculture may comprise promoting plant growth. Also disclosed is a method for regulating the growth of a plant, comprising applying a plant-growth-regulating amount of a compound, salt, solvate, or formulation of the present disclosure. Plant growth may be increased by at least about 5%, such as 10%, 15%, 20%, 25%, 30%, or 50%. In at least one embodiment, plant growth may be increased by at least about 60%, 70%, 80%, 90%, 95%, 100% or more.

In at least one embodiment, the life of the contacted plant is extended as compared to a substantially identical but otherwise uncontacted plant, the wilting of the contacted plant is reduced or delayed as compared to a substantially identical but otherwise uncontacted plant, the turgidity of the contacted plant is prolonged or maintained as compared to a substantially identical but otherwise uncontacted plant, the loss of one or more petals of the contacted plant is reduced or delayed as compared to a substantially identical but otherwise uncontacted plant, the chlorophyll content of the contacted plant is maintained as compared to a substantially identical but otherwise uncontacted plant, the loss of the chlorophyll content of the contacted plant is reduced or delayed as compared to a substantially identical but otherwise uncontacted plant, the chlorophyll content of the contacted plant is increased as compared to a substantially identical but otherwise uncontacted plant, a salinity tolerance of the contacted plant is increased as compared to a substantially identical but otherwise uncontacted plant, the water consumption of the contacted plant is reduced as compared to a substantially identical but otherwise uncontacted plant, the drought tolerance of the contacted plant is increased as compared to a substantially identical but otherwise uncontacted plant, the pest resistance of the contacted plant is increased as compared to a substantially identical but otherwise uncontacted plant, the pesticides consumption of the contacted plant is reduced as compared to a substantially identical but otherwise uncontacted plant, or any combination thereof.

Further the present disclosure relates to a method for promoting the germination of a seed, comprising applying a seed-germination-promoting amount of a compound, salt, solvate, or formulation of the present disclosure to a seed.

In another aspect, the present disclosure provides for a method controlling weeds comprising applying a seed-germination-promoting amount of a compound salt, solvate, or formulation of the present disclosure to a seed.

It is to be understood that this disclosure is not limited to the particular embodiments described herein. As will be apparent to those of ordinary skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other acceptable order.

EXAMPLES

Example 1—Synthesis of compound MBS-127 (3-(4-Methyl-5-oxo-2,5-dihydro-furan-2-yloxy)-acrylic acid methyl ester)

Step 1: Preparation of Intermediate 4 (ethyl 4-acetoxy-4-chloro-2-hydroxy-2-methylbutanoate)

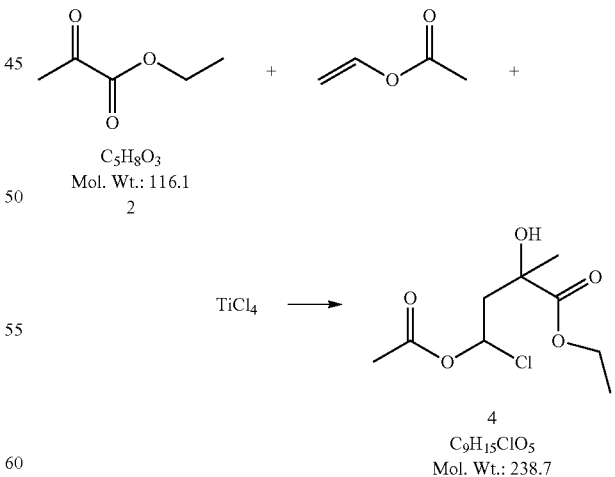

A 1-liter 3-neck flask equipped with an overhead stirrer was flushed with nitrogen for 10 minutes. 500 mL dichloromethane (DCM) was charged and TiCl$_4$ (35.0 mL, 0.32 mol, 1.0 eq) was added via syringe. The resulting solution was cooled to −1° C. Ethyl pyruvate (37.0 g, 0.32 mol, 1.0 eq) and vinyl acetate (27.8 g, 0.32 mol, 1.0 eq) in 120 mL DCM was added dropwise over 2 hours. A suspension was formed during the addition and replaced with a yellow solution. After addition, the reaction was stirred at 0° C. for 2 hours. The reaction was quenched with 240 mL water dropwise at 0° C. The organic layer was separated and the aqueous layer was extracted with 2×100 mL DCM. The combined DCM was washed with 2×150 mL brine and dried over MgSO$_4$, filtered. Solvent was removed to give a golden oil. The crude product was stored in a –10° C. freezer and used without further purification.

Step 2: Preparation of Intermediate 5
(5-hydroxy-3-methylfuran-2(5H)-one)

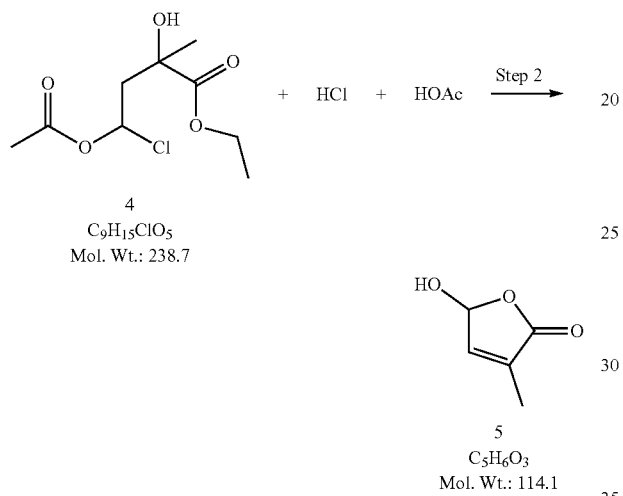

12 N HCl (34 mL) and HOAc (34 mL) were added to the solution of crude product 4 in 700 mL of 200 proof ethanol to give a golden solution. The reaction was refluxed for 4 hours and 860 mL water was added. 960 mL solvent was removed under reduced pressure and the reaction mixture was refluxed for one hour. The cooled reaction was extracted with ethyl acetate (6×200 mL) until no product was observed in the aqueous layer via thin layer chromatography (TLC). The combined ethyl acetate was washed with brine (100 mL), dried over MgSO$_4$, filtered and condensed. The residue was loaded on silica gel and eluted with 1:1 heptane:EA to give 15.0 g yellow solid which was slurried in 60 mL heptane for 20 min to give the product as a yellow solid. The solid was slurried in 60 mL heptane, filtered to give the product as a pale yellow solid (14.6 g).

Step 3: Preparation of MBS-127 (3-(4-Methyl-5-oxo-2,5-dihydro-furan-2-yloxy)-acrylic acid methyl ester)

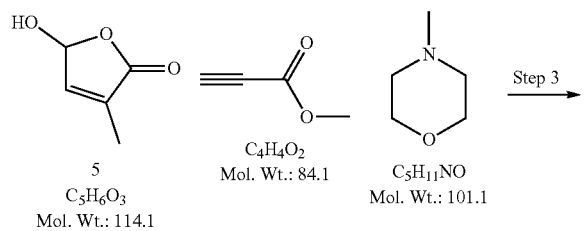

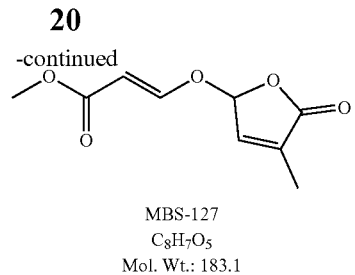

MBS-127
C$_8$H$_7$O$_5$
Mol. Wt.: 183.1

Figure 8:
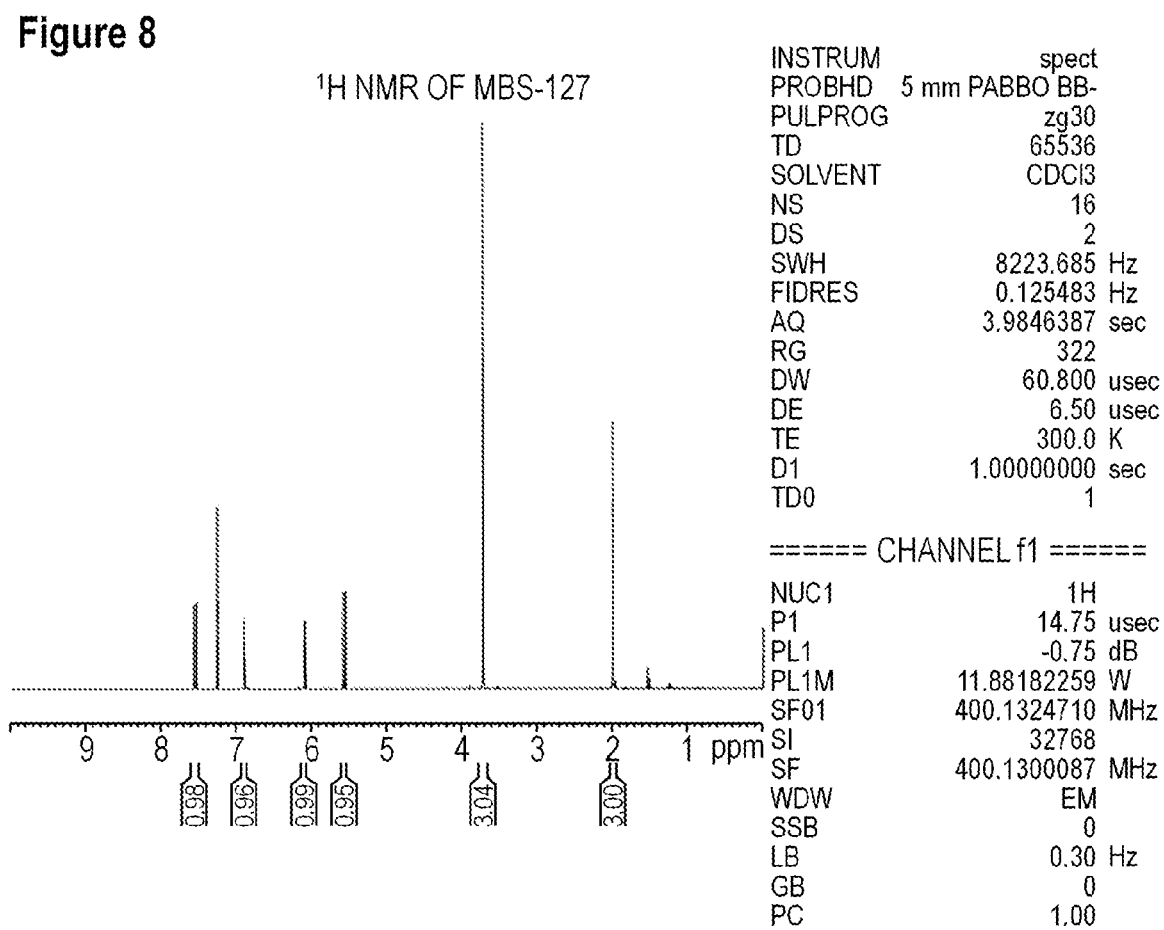
FIG. 8 is a $^1$H NMR spectrum of MBS-127 produced with a chloroform solvent (CDCl3) in a 400 MHz Bruker spectrometer.

Under nitrogen, methyl propionate (1.85 g, 22 mmol, 1 eq) and 4-methyl morpholine (2.2 g, 22 mmol, 1 eq) were added to the solution of compound 5 (5.0 g, 44 mmol, 2 eq) in 50 mL dry tetrahydrofuran (THF) at 0° C. The reaction was stirred at 0° C. for 15 min then stirred at room temperature (RT overnight. The reaction was condensed and 100 ml NH$_4$Cl was added, and then extracted with ethyl acetate (3×100 mL). The combined organic was washed with brine (100 mL), dried over MgSO$_4$, filtered, and condensed. The crude product was purified by chromatography using 2:1 heptane:ethyl acetate (EA) to afford the product as a pale yellow solid, a representative NMR of which is shown in FIG. 8.

Example 2—Synthesis of Compound MBS-128

Step 1: Preparation of MBS-128 (methyl (E)-3-((2,4-dimethyl-5-oxo-2,5-dihydrofuran-2-yl)oxy)acrylate)

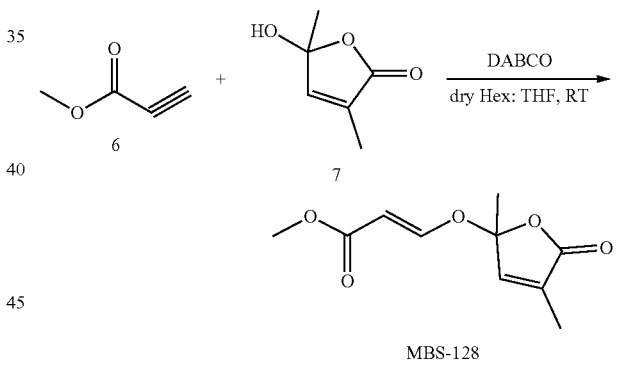

Figure 9:
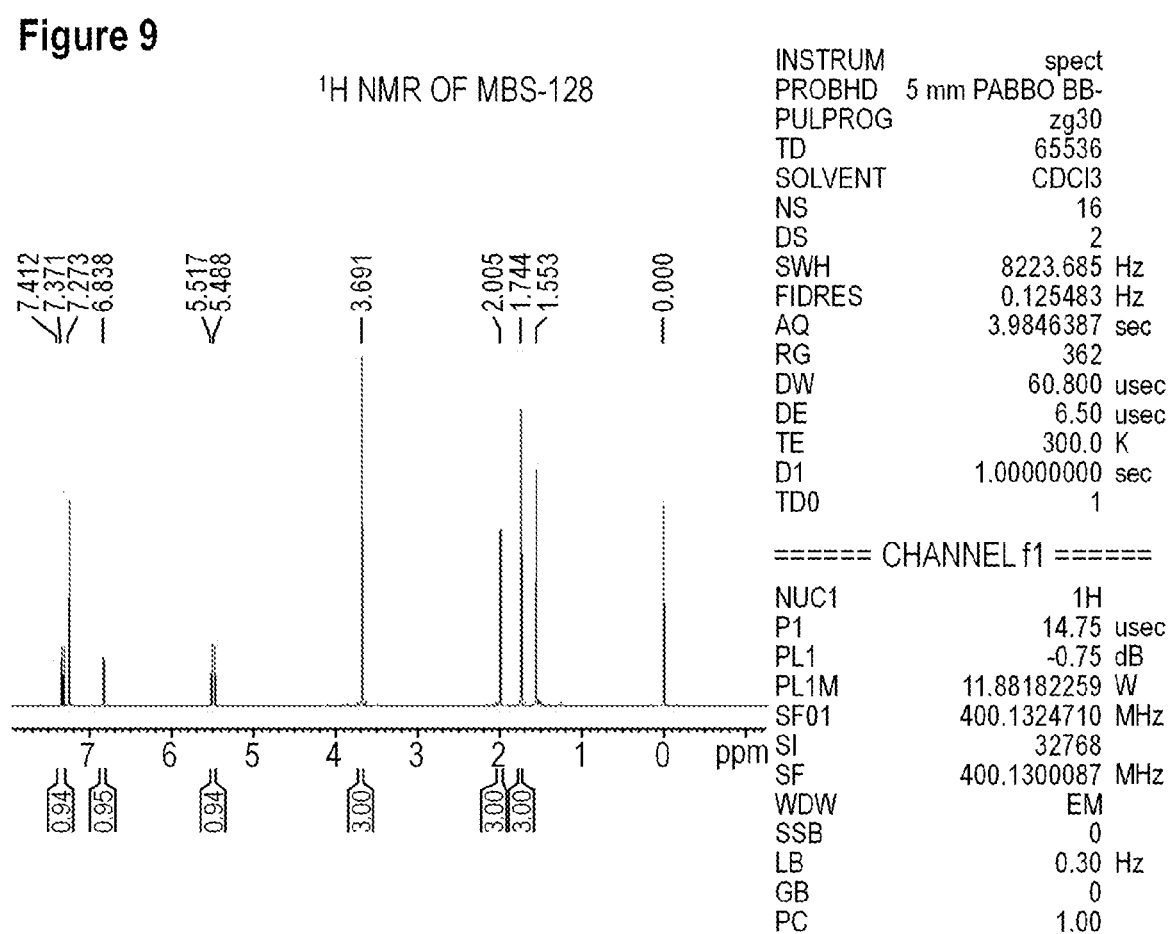
FIG. 9 is a $^1$H NMR spectrum of MBS-128 produced with a chloroform solvent (CDCl3) in a 400 MHz Bruker spectrometer.

A 250 mL dry round bottom flask was charged with 5-Hydroxy-3,5-dimethyl-5H-furan-2-one (7, 5 g, 39 mmol, 1 eq) and 1,4-diazabicyclo[2.2.2]octane (DABCO) (0.437 g, 3.9 mmol, 0.1 eq), to this reaction flask 90 mL of dry hexanes and anhydrous THF were added in 6:1 ratio under nitrogen. After 5 minutes of stirring, methyl propiolate (6, 5.16 mL, 58.5 mmol, 1.5 eq) was added to the reaction mixture in 6 portions for every 5 minutes and then the reaction mixture is stirred under nitrogen at RT overnight (12 hours). After confirming the formation of product by GCMS, the reaction mixture was concentrated under vacuum to get 9.43 g of crude material. The crude material was dissolved in minimum amounts of DCM to form a white precipitate which was removed through filtration. The filtrate was concentrated and purified over silica using a mixture of ethyl acetate in heptanes to get 2.2 grams of pure compound 2 as pale yellow oil, a representative NMR of which is shown in FIG. 9.

Example 3—Strigolactone-Like Activity of the Disclosed Compounds

The ability of a novel compound to act in an equivalent manner to a native strigolactone can be assessed by testing its ability to complement phenotypes caused by mutations that disrupt the natural biosynthesis of strigolactones within the plant. In *Arabidopsis thaliana*, a knock out mutation in the MORE AXILLARY BRANCHING 4 (MAX4) gene results in a complete interruption of strigolactone biosynthesis that exhibits ectopic shoot branching (Gong, L., et al., "Genes involved in the synthesis and signaling pathway of strigolactone, a shoot branching inhibitor," *Biologia Plantarum* (2012) Vol. 56 (2), pp. 210-214) (Sorefan, K., et al., "MAX4 and RMS1 are orthologous dioxygenase-like genes that regulate shoot branching in *Arabidopsis* and pea," *Genes & Development* (2003), Vol. 17 (12), pp. 1469-1474). The compounds MBS-127 and MBS-128 are both effective in reducing the ectopic branching phenotype observed in a max4 mutant line in *Arabidopsis thaliana* (FIG. 1).

The metric used to assess branching was the number of secondary bolts over 0.5 cm in length in plants that have a primary bolt over 6 cm long. Assessments were made after treatments with solution containing control solvent DMSO, the strigolactone molecule MBS-127 in DMSO, and the strigolactone molecule MBS-128 in DMSO as detailed below. Stratified *A. thaliana* homozygous max4 knockout mutant seeds were planted on rockwool plugs suspended above reservoirs of 0.5× Hoagland's solution. The plants were grown under 16 hours of light per day at 22° C. and at 19° C. during the nights throughout the experiment. After 3 weeks of growth, the treatment mixture described was added to the reservoir solution. The final concentration of DMSO in the reservoirs was 0.1%, and the final concentration of the compounds MBS-127 and MBS-128 was 10 µM. Solutions were replaced weekly, maintaining a consistent treatment scheme. After a further 3 weeks, counts were made of the number of secondary bolts that were over 0.5 cm long that occurred on plants with a primary bolt over 6.0 cm long. Results of this experiment are shown in FIG. 1.

Figure 2:
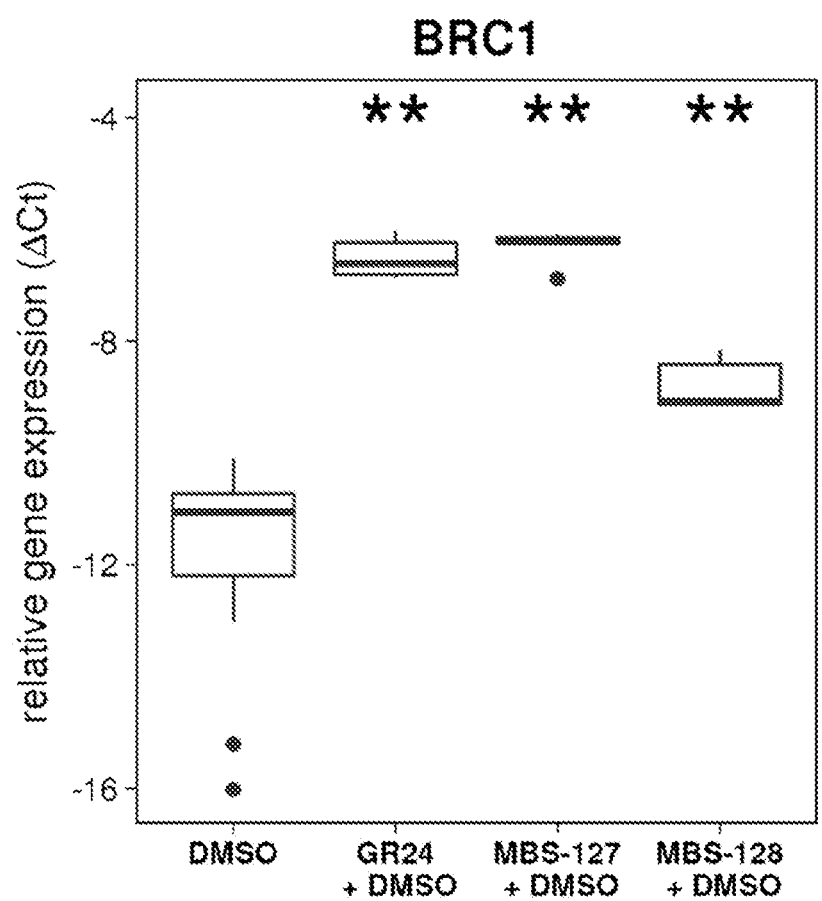

Another experiment was performed to consider an aspect of molecular signal transduction. A number of genes in *Arabidopsis thaliana* are well known downstream signaling targets of the native strigolactone pathway. This includes a key regulator of shoot branching, BRANCHED1 (BRC1) (Wang, L., et al., "Strigolactone Signaling in *Arabidopsis* Regulates Shoot Development by Targeting D53-Like SMXL Repressor Proteins for Ubiquitination and Degradation," The Plant Cell (2015) Vol. 27(11), pp. 3128-3142). The compounds MBS-127 and MBS-128 both induced expression of the BRC1 gene similarly to the previously described strigolactone, GR24. This indicates that the compounds MBS-127 and MBS-128 act through the canonical strigolactone signaling pathway to repress ectopic branching seen in the max2 mutant (FIG. 2).

In this experiment sterilized and stratified seeds of the *A. thaliana* Columbia (Col-0) were planted on growth media (Murashige and Skoog (MS) M404 with vitamins (2.2 g/L), 0.5% sucrose, 0.05% MES hydrate, 0.6% PhytoBlend™) for eight days in a growth chamber under 16 hours of light per day at 22° C. and 19° C. nights. The seedlings were sprayed with a foliar application of water and 0.05% AdMax90 containing the control solvent DMSO, the strigolactone molecule MBS-127 in DMSO, or the strigolactone molecule MBS-128 in DMSO. The concentration of DMSO in the treatment material was 0.4% and the tested strigolactones were present in a concentration of 260 µM. 24 hours later the shoots were harvested and frozen on liquid nitrogen. Total RNA was extracted and RT-PCR quantification was performed using kits from Macherey-Nagel and Bioline and an ABI 7900HT instrument. Primers were designed with NCBI's Primer-BLAST tool and ordered from Integrated DNA Technologies. Results of this experiment are shown in FIG. 2.

Figure 3:
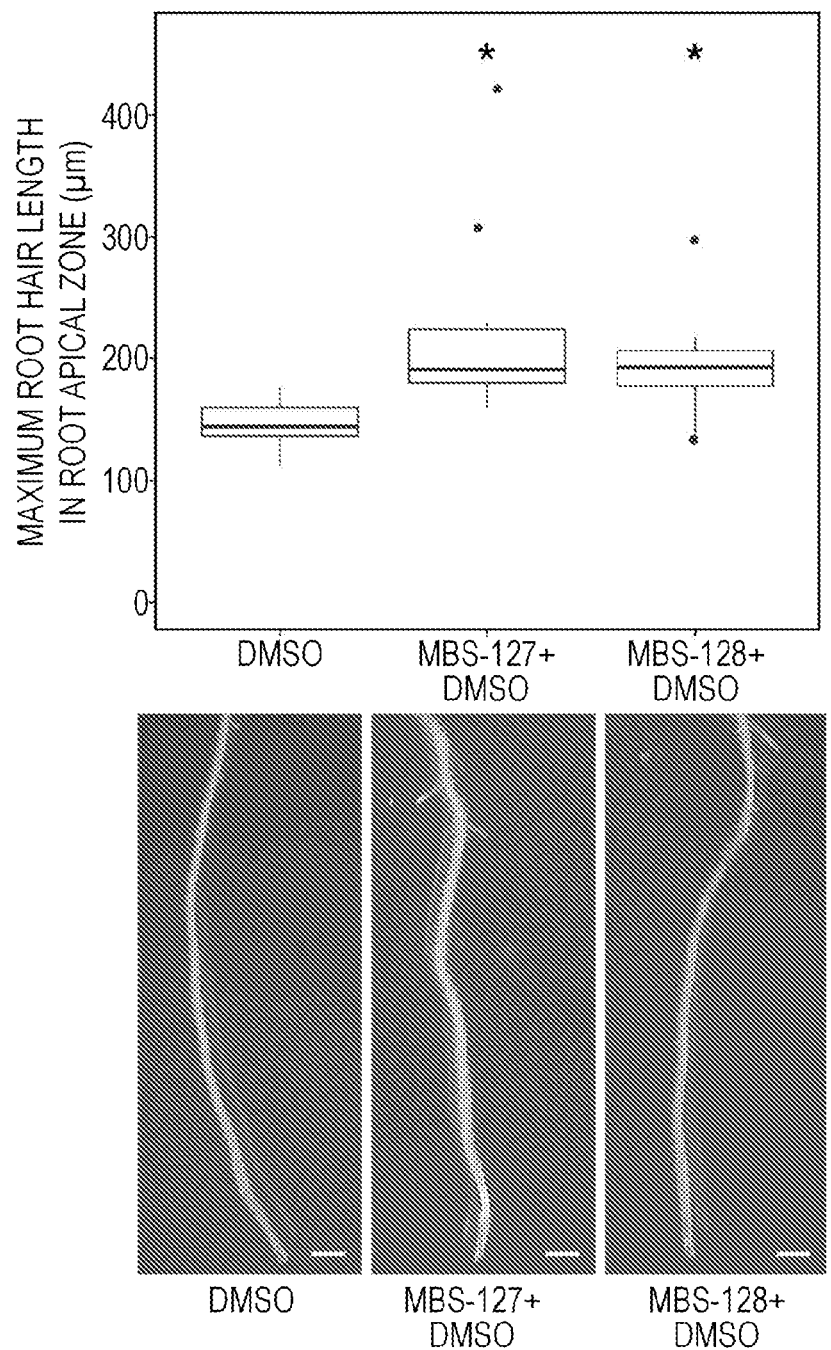
FIG. 3 is a boxplot representing the maximum root hair length in the root apical zone of *A. thaliana* treated with the control solvent DMSO, strigolactone molecule MBS-127 in DMSO, and strigolactone molecule MBS-128 in DMSO. Stars indicate significant differences relative to the DMSO control (*: adjusted p-value<0.01; p-values adjusted for multiple-hypothesis testing); non-parametric Mann-Whitney U-tests were used to assess significance. Representative images show root hairs in the root apical zone of plants treated with the control solvent DMSO, the strigolactone molecule MBS-127 in DMSO, and the strigolactone molecule MBS-128 in DMSO. Scale bars equal 1 mm.
Figure 4:
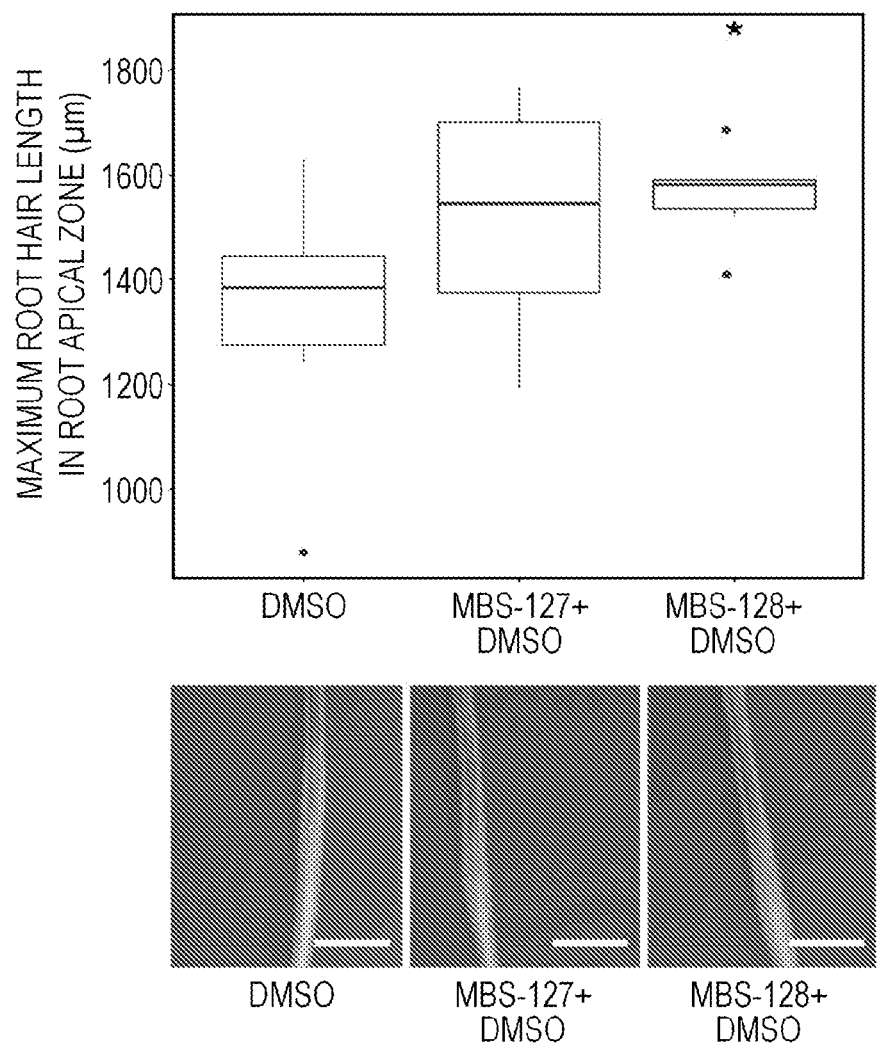
FIG. 4 is a boxplot graph representing the distribution of maximum root hair length in the root apical zone of *Z. mays* with the control solvent DMSO, strigolactone molecule MBS-127 in DMSO, and strigolactone molecule MBS-128 in DMSO. Stars indicate significant differences relative to the DMSO control (*: adjusted p-value<0.1; p-values were adjusted for multiple-hypothesis testing using a Bonferroni correction). Representative images show root hairs in the root apical zone of plants treated with the control solvent DMSO, strigolactone molecule MBS-127 in DMSO, and strigolactone molecule MBS-128 in DMSO. Scale bars equal 10 mm.

Example 4—Improved Root Architecture in *Arabidopsis thaliana* and *Zea mays* Under Various Nutrient Conditions Root proliferation is critical for plants in exploiting the soil volume for available water and uptake of mineral elements (Wang Y., T.-K. K. "Vigorous root growth is a better indicator of early nutrient uptake than root hair traits in spring Wheat Grown under low fertility," *Frontiers in Plant Science* (2016), Vol. 7 (865), doi: 10.3389/fpls.2016.00865), and root hair elongation and abundance has special importance in these processes (Haling, R. E., et al., "Root hairs improve root penetration, root-soil contact, and phosphorus acquisition in soils of different strength," *Journal of Experimental Botany* (2013) Vol. 64 (12), pp. 3711-3721). The strigolactone compounds MBS-127 and MBS-128 were found to enhance root hair elongation and proliferation in both *A. thaliana* (FIG. 3) and *Z. mays* (FIG. 4). The maximum root hair length in the root apical zone of *A. thaliana* treated with the control solvent DMSO, strigolactone molecule MBS-127 in DMSO, and strigolactone molecule MBS-128 in DMSO.

In this experiment sterilized seeds of the *A. thaliana* Columbia (Col-0) ecotype were planted on growth media (Murashige and Skoog (MS) M404 with vitamins (2.2 g/L), 0.5% sucrose, 0.05% MES hydrate, 0.6% PhytoBlend™) and grown for nine days. The seedlings were then transplanted to phosphate limiting media (MS M407 modified basal salt without nitrogen, phosphorous, or potassium (610 mg/L), 0.05% MES hydrate, supplemented with potassium phosphate (17 mg/L), ammonium nitrate (825 mg/L), potassium nitrate (950 mg/L), and 1.5% Bacto™ Agar) containing the control solvent DMSO (0.1%), the strigolactone molecule MBS-127 (2.5 µM) in DMSO (0.1%), or the strigolactone molecule MBS-128 (2.5 µM) in DMSO (0.1%), and grown for 16 days. Plants were continuously grown under 16 hours of light (150 µmol m$^{-2}$ s$^{-1}$) per day at 21° C. in the day and at 19° C. in the night. Images of each plant (n=12) were taken after seven days of growth on the phosphate limiting media. The longest root hair, within the root apical zone, was measured from the images using ImageJ. Mann-Whitney U-tests were used to assess the difference between the longest root hair of the plants treated with the control solvent DMSO to strigolactone molecule MBS-127 in DMSO or to strigolactone molecule MBS-128 in DMSO; tests were corrected together for multiple-hypothesis testing using a Bonferroni correction. Results of this experiment are shown in FIG. 3.

Similarly, compounds MBS-127 and MBS-128 were found to induce root hair elongation in *Z. mays* under various nutrient levels (shown here under insufficient phosphate conditions). Results of this experiment are shown in FIG. 4.

Figure 5:
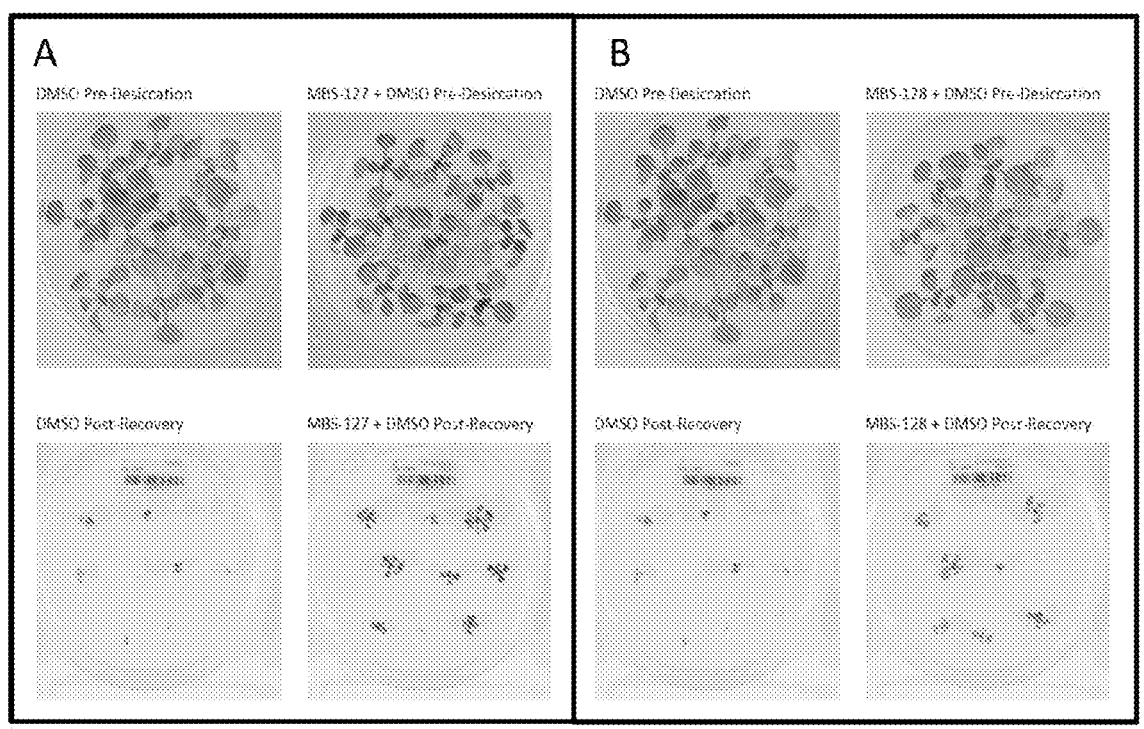
FIG. 5 shows representative images of *A. thaliana* seedlings treated with the control solvent DMSO, A) the formulation A in DMSO, and B) formulation B in DMSO immediately before being subjected to a desiccation stress (TOP) and one week after recovering from desiccation stress (BOTTOM).

Example 5—Protecting *A. thaliana* and *S. lycopesrsicum* from Abiotic Stress Post germination desiccation is an extreme form of dehydration which can be used as a survival assay for testing abiotic stress tolerance in plants. While desiccation stress is distinct from the gradual onset of drought typically experienced in an agricultural setting, the response in the plant has many commonalities across both cases (Fernando, V. C., & Schroeder, D. F. "Role of ABA in *Arabidopsis* Salt, Drought, and Desiccation Tolerance," (2016), pp. 507-518), and increased tolerance in one case can often predict tolerance in the other. Endogenous strigolactones have previously been shown to play a native role in the response to abiotic stress (Ha, C. V, et al. "Positive regulatory role of strigolactone in plant responses to drought and salt stress," *Proceedings of the National Academy of Sciences of the United States of America* (2014) Vol. 111 (2), pp. 851-856). Here, compounds MBS 127 and MBS-128 were found to increase the survival and vigor of *A. thaliana* seedlings that have been exposed to a severe desiccation stress (FIG. 5).

In this experiment sterilized and stratified seeds of the *A. thaliana* Columbia (Col-0) were planted on growth media (Murashige and Skoog (MS) M404 with vitamins (2.2 g/L), 0.5% sucrose, 0.05% MES hydrate, 0.6% PhytoBlend™) and grown for nine days in a growth chamber with continuous light at 22° C. The seedlings were then transplanted to same media supplemented with the control solvent DMSO, strigolactone molecule MBS-127 in DMSO, or strigolactone molecule MBS-128 in DMSO. The final concentration of DMSO in the media was 0.4% and the concentration of MBS-127 and MBS-128 was 50 µM. After three days of growth on the treatment media the seedlings were photographed and then transplanted to dry filter paper and subjected to 4 hours of desiccation stress. Then, seedlings were transplant back to plates with the original media type and allowed to recovery for seven days before being photographed. Results of this experiment are shown in FIG. 5.

Figure 6:
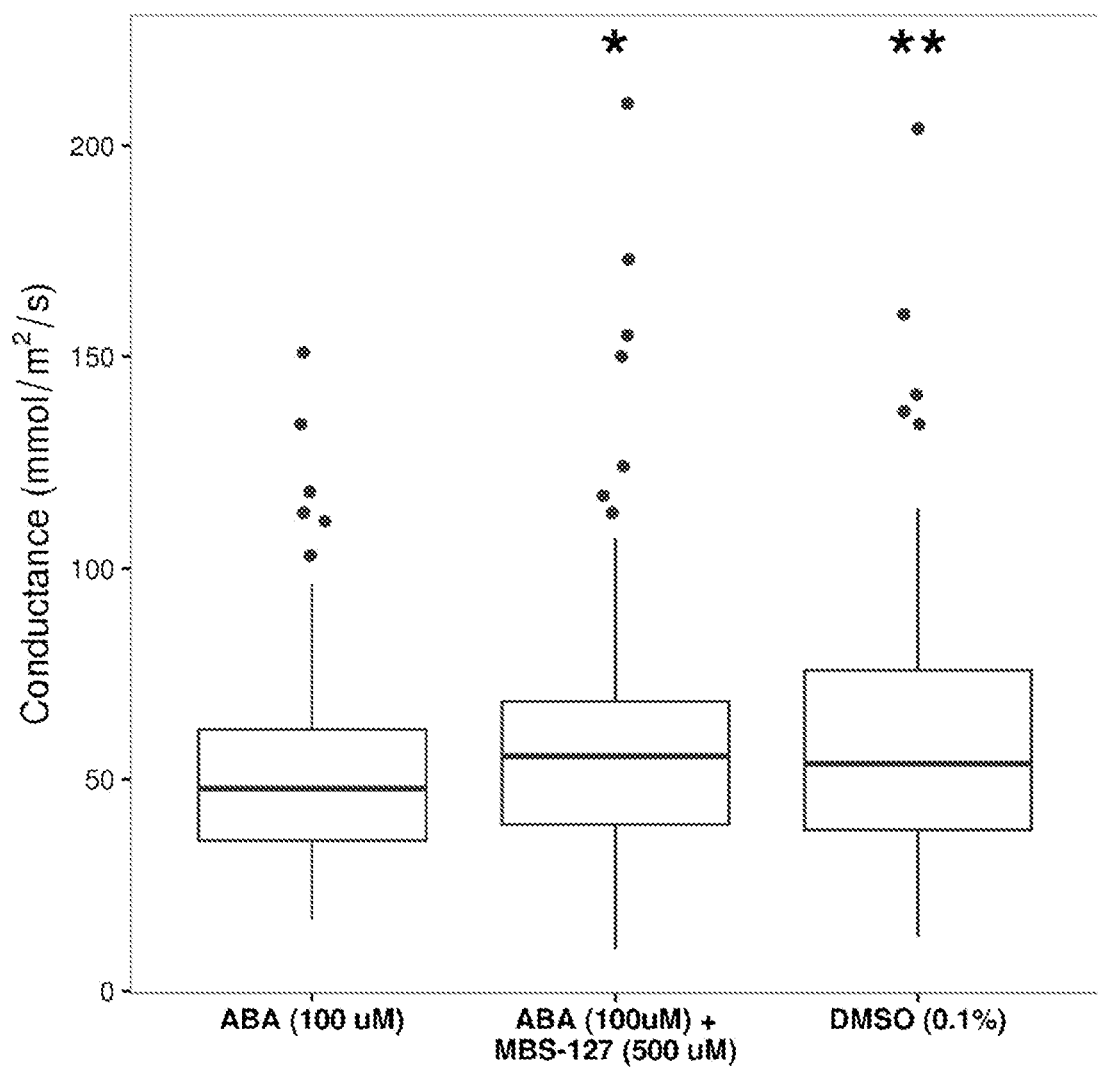
FIG. 6 is a boxplot showing the distribution of tomato (*S. lycopersicum* cv. Micro-Tom) stomatal conductance (mmol/m$^2$/s) measurements taken via LI-6400XT, plotted by treatment. Plants treated with strigolactone molecule MBS-127 prior to treatment with abscisic acid (ABA) show increased stomatal conductance, as measured by gas exchange with the LI-6400XT, compared to plants treated with ABA alone. Stars indicate significant differences relative to ABA (*: adjusted P<0.05, **: adjusted P<0.01; p-values were adjusted for multiple-hypothesis testing using a Bonferroni correction).

An early response and critical component of abiotic stress response signaling in plants is the production and transport of the phytohormone abscisic acid (ABA) (Kuromori, T., et al., "ABA Transport and Plant Water Stress Responses," *Trends in Plant Science* (2018) Vol. 23 (6), pp. 513-522). Efforts to utilize ABA as a solution for crop protection chemistry has been hampered by deleterious effects on growth and yield in response to exogenous ABA application (Du, Y.-L., et al., "Exogenous abscisic acid reduces water loss and improves antioxidant defence, desiccation tolerance and transpiration efficiency in two spring wheat cultivars subjected to a soil water deficit," *Functional Plant Biology* (2013) Vol. 40 (5), pp. 494-506) (Ahmadi, A., Baker, D. "Effects of abscisic acid (ABA) on grain filling processes in wheat," *Plant Growth Regulation* (1999) Vol. 28 (3), pp. 187-197) (Ruggiero B., et al., "Uncoupling the Effects of Abscisic Acid on Plant Growth and Water Relations. Analysis of sto1/nced3, an Abscisic Acid-Deficient but Salt Stress-Tolerant Mutant in *Arabidopsis*," *Plant Physiology* (2004) Vol. 136 (2), pp. 3134-3147). A specific effect of exogenous ABA treatment is the reduction in stomatal aperture and concomitant reduction of evapotranspiration and gas exchange (Astacio, M. G., & Iersel, M. W. "Determining the Effects of Abscisic Acid Drenches on Evapotranspiration and Leaf Gas Exchange of Tomato," *Hortscience* (2011) Vol. 46 (11), pp. 1512-1517). While the compounds of the formulas described herein are able to protect plants from abiotic stress, they are also able to modulate aspects of the response to ABA in *Solanum lycopersicum* (FIG. 6). Specifically, strigolactone molecule MBS-127 was found to protect against the drought stress response related reduction in leaf conductance induced by ABA.

In this experiment sterilized seeds of *S. lycopersicum* cv. Micro-Tom were planted into Berger BM2 Seed Germination and Propagation Mix supplied with 1.6 g/L of 20-20-20 Peters Professional@ general purpose fertilizer. Plants were grown under 16 hours of light per day (150 µmol m$^{-2}$ s$^{-1}$), at 21° C. in the day and at 19° C. in the night, with humidity set at 65%. The experimental design included constrained randomized blocks based on treatments. After 18 days of growth, treatments with the control solvent DMSO (0.1%), ABA (100 µM) in DMSO (0.1%), or the strigolactone molecule MBS-127 (500 µM) in DMSO (0.1%) were applied. ABA (100 µM) in DMSO (0.1%) was applied one hour later. All treatments were applied in 0.5 mL aqueous carrier volume per plant. One day before the gas exchange measurements were taken, the plants were placed in the dark with the same temperature and humidity settings as described. After 21 days of growth the plants were screened with LI-6400XT machines, using a spot measurement of gas exchange parameters in the leaf (photosynthetically active radiation (PAR) was set at 0 µmol m$^{-2}$ s$^{-1}$, reference $CO_2$ concentration was maintained at 400 µmol mol$^{-1}$, humidity was set at 63%±2%, and the leaves were acclimated in the instrument until measurements stabilized for photosynthesis (slope<0.01) and conductance (slope<0.05)). The entire experiment was repeated three times.

Conductance values were log 10 transformed (per results of a Box-Cox transformation assessment) to better meet the assumptions of regression. Treatment effects on transformed conductance values were assessed by fitting a linear mixed model in R, using the lmer function from the lme4 package (Bates, D., et al. "Fitting Linear Mixed-Effects Models Using lme4," *Journal of Statistical Software* (2015) Vol. 67 (1), pp. 1-48), with treatment as a fixed factor, and Latin square row, Latin square column, and LI-6400XT machine as random factors. Results of this experiment are shown in FIG. 6.

Example 6—Increased Water Uptake, Apical Transport, and Leaf Conductance in *Z. mays*

Figure 7:
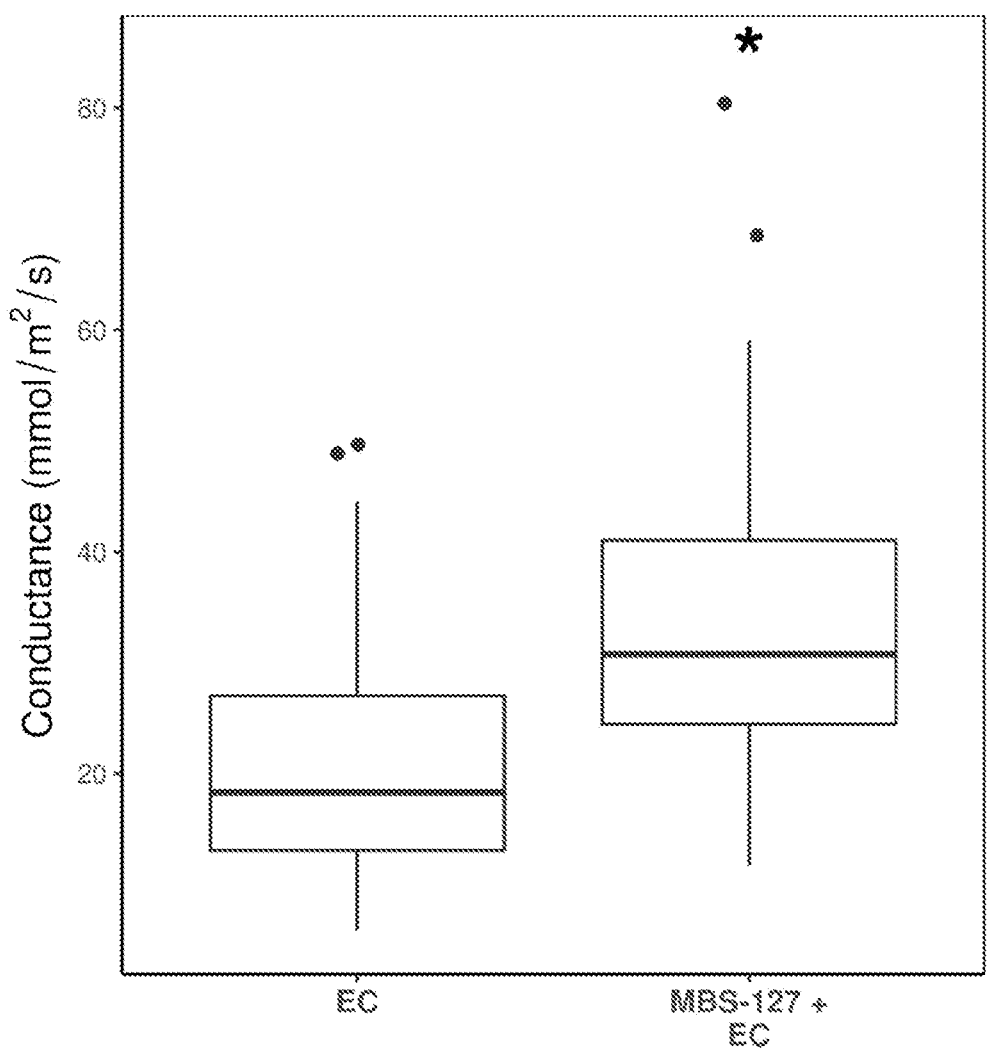
FIG. 7 is a boxplot representing the distribution of stomatal conductance (mmol/m$^2$/s) measurements taken via LI-6400XT on *Zea mays* plants treated with EC formulation blank and Crop Oil Concentrate (control; EC) or strigolactone molecule MBS-127, EC formulation blank and Crop Oil Concentrate (MBS-127+EC). Plants treated with strigolactone molecule MBS-127 showed a 60% increase in stomatal conductance compared to the control group. Letters define significant classes with P<0.05. Points show observations falling outside of the whiskers and have been jittered along the x-axis to avoid overlap.

Water transport is closely intertwined with many vital plant processes, including photosynthesis, translocation, mineral nutrition, growth, and plays a critical role in defining the yield potential of a crop field (Azizian, A., & Sepaskhah, A. R. "Maize response to water, salinity and nitrogen levels: yield-water relation, water-use efficiency and water uptake reduction function," *International Journal of Plant Production* (2014) Vol. 8(2), pp. 183-214). The compounds of formulas described herein induce increased leaf conductance in the leaves of intact *Z. mays* plants (FIG. 7). Plants treated with strigolactone molecule MBS-127 showed a 60% increase in stomatal conductance compared to the control group.

In this experiment maize (*Zea mays* Dekalb Hybrid DKC68-26RIB) plants were grown in a greenhouse in one-gallon pots filled with Sunshine #2 soil-less growing mix. Plants were irrigated four times daily for with standard greenhouse fertilizer (N 228 ppm, P 140 ppm, K 309 ppm, Ca 200 ppm, Mg 44 ppm, S 68 ppm, Zn 5 ppm). Individual irrigation times varied depending on the age of the plants and external temperature but ranged from two to five minutes. Plants were grown with the temperature ranging from at 20° C. during the night to 33° C. during the range with the humidity varying between 30 to 80%. The experimental design included constrained randomized blocks based on treatments. At the time of spraying (16 days after sowing), plants were selected for uniform plant size. These plants were then sprayed that afternoon. Compounds of the present disclosure were formulated into the form of an methyl ester based EC formulation (EC) at a working concentration of a 1%. The EC was then diluted with water and after the addition of 1% JHT Crop Oil Concentrate (COC; JR Simplot), sprayed onto the green parts of the maize plants. Material was delivered at an application rate of 2 grams of the compound of interest/acre within a carrier volume of 32 gallons/acre using a DeVries Generation III Spray Chamber equipped with a TeeJet 8002E flat fan spray nozzle driven by compressed air at a pressure of 40 PSI and a nozzle speed of 1.2 MPH. Control plants were treated in the same manner but with the EC plus 1% COC solely. The next morning (17 days after sowing), plants were screened to determine stomatal conductance measurements using the LI-6400XTR by taking two spot gas exchange measurements on the V5 leaf. Photosynthetically active radiation (PAR) was set at 0 μmol m-2 s-1, reference CO2 concentration was maintained at 400 μmol mol-1, humidity was set at 60%±3%. Leaves were acclimated within the LI6400XTR sensor head until gas exchange measurements had stabilized for conductance and then the conductance for that leaf determined. Results of this experiment are shown in FIG. 7.

In some embodiments, the present disclosure is directed to:

1. A compound of Formula (I):

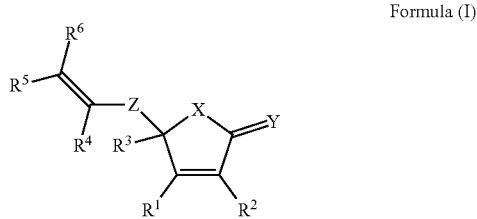

Formula (I)

wherein

X, Y, and Z are independently O, S, or —$NR^7$;

$R^1$, $R^2$, $R^3$, $R^4$, $R^5$, and $R^6$ are each independently H, amino, halo, substituted or unsubstituted alkyl, substituted or unsubstituted aryl, substituted or unsubstituted heteroalkyl, substituted or unsubstituted heteroaryl, substituted or unsubstituted arylalkyl, substituted or unsubstituted cycloalkyl, substituted or unsubstituted heterocycloalkyl, —$OR^8$, —$SR^8$, —$C(O)R^8$, —$C(O)OR^8$, —$C(S)R^8$, —$C(S)OR^8$, —$C(S)SR^8$, —$C(O)NR^8$; or $R^4$ and $R^5$ together with the carbons to which they are attached form a cycloalkyl, cycloalkenyl, heterocycloalkyl, or heterocycloalkenyl ring, which is optionally substituted with one or more substituents selected from amino, halo, alkyl, cycloalkyl, aryl, and oxo; and $R^7$ and $R^8$ are each independently H, substituted or unsubstituted alkyl, substituted or unsubstituted aryl, substituted or unsubstituted heteroalkyl, substituted or unsubstituted heteroaryl, substituted or unsubstituted arylalkyl, substituted or unsubstituted cycloalkyl, or substituted or unsubstituted heterocycloalkyl;

or a salt or solvate thereof.

2. The compound of embodiment 1, wherein X, Y, and Z are O.

3. The compound of embodiment 1, wherein Y and Z are O; and X is —$NR^7$.

4. The compound of embodiment 1, wherein X, Y, and Z are O; $R^1$, $R^2$, $R^3$, $R^4$, and $R^5$ are independently H, substituted or unsubstituted alkyl, or substituted or unsubstituted aryl; and $R^6$ is —$C(O)OR^8$, —$C(S)R^8$, —$C(S)OR^8$, —$C(S)SR^8$, —$C(O)NR^8$.

5. The compound of embodiment 1, wherein X, Y, and Z are O; $R^1$, $R^2$, $R^3$, and $R^6$ are independently H, substituted or unsubstituted alkyl, or substituted or unsubstituted aryl; and $R^4$ and $R^5$ together with the carbons to which they are attached form a cycloalkyl, cycloalkenyl, heterocycloalkyl, or heterocycloalkenyl ring, which is optionally substituted with one or more substituents selected from amino, halo, alkyl, cycloalkyl, aryl, and oxo.

6. The compound of embodiment 1, wherein X is —$NR^7$; Y and Z are O; R, $R^2$, $R^3$, $R^4$, and $R^5$ are independently H, substituted or unsubstituted alkyl, or substituted or unsubstituted aryl; and $R^6$ is —$C(O)OR^8$, —$C(S)R^8$, —$C(S)OR^8$, —$C(S)SR^8$, —$C(O)NR^8$.

7. The compound of embodiment 1, wherein X is —$NR^7$; Y and Z are O; $R^1$, $R^2$, $R^3$, and $R^6$ are independently H, substituted or unsubstituted alkyl, or substituted or unsubstituted aryl; $R^4$ and $R^5$ together with the carbons to which they are attached form a cycloalkyl, cycloalkenyl, heterocycloalkyl, or heterocycloalkenyl ring, which is optionally substituted with one or more substituents selected from amino, halo, alkyl, cycloalkyl, aryl, and oxo; and $R^7$ is H, substituted or unsubstituted alkyl, or substituted or unsubstituted aryl.

8. The compound of embodiment 1, wherein X, Y, and Z are O; $R^1$, $R^2$, $R^3$, $R^4$, and $R^5$ are independently H, or alkyl; $R^6$ is —$C(O)OR^8$, —$C(S)R^8$, —$C(S)OR^8$, —$C(S)SR^8$, —$C(O)NR^8$; and $R^8$ is H, substituted or unsubstituted alkyl, or substituted or unsubstituted aryl.

9. The compound of embodiment 1, wherein X is —$NR^7$; Y and Z are O; R, $R^2$, $R^3$, $R^4$, and $R^5$ are independently H, or alkyl; $R^6$ is —$C(O)OR^8$, —$C(S)R^8$, —$C(S)OR^8$, —$C(S)SR^8$, —$C(O)NR^8$; $R^7$ is H, substituted or unsubstituted alkyl, or substituted or unsubstituted aryl; and $R^8$ is H, substituted or unsubstituted alkyl, or substituted or unsubstituted aryl.

10. The compound of embodiment 1, wherein X, Y, and Z are O; $R^1$, $R^2$, $R^3$ are independently H or alkyl; $R^4$ and $R^5$ together with the carbons to which they are attached form a cycloalkyl, cycloalkenyl, heterocycloalkyl, or heterocycloalkenyl ring, which is optionally substituted with one or more substituents selected from amino, halo, alkyl, cycloalkyl, aryl, and oxo; and $R^8$ is H, substituted or unsubstituted alkyl, or substituted or unsubstituted aryl.

11. The compound of embodiment 1, wherein X is —$NR^7$; Y and Z are O; $R^1$, $R^2$, $R^3$, and $R^6$ are independently H, or alkyl; $R^4$ and $R^5$ together with the carbons to which they are attached form a cycloalkyl, cycloalkenyl, heterocycloalkyl, or heterocycloalkenyl ring, which is optionally substituted with one or more substituents selected from amino, halo, alkyl, cycloalkyl, aryl, and oxo; and $R^8$ is H, substituted or unsubstituted alkyl, or substituted or unsubstituted aryl.

12. The compound of embodiment 1, wherein X, Y, and Z are O and $R^1$ is methyl.

13. The compound of embodiment 1, wherein X, Y, and Z are O; and $R^2$ is methyl.

14. The compound of embodiment 1, wherein X, Y, and Z are O; and $R^3$ is methyl.

15. The compound of embodiment 1, wherein X, Y, and Z are O; and $R^1$, $R^2$, and $R^3$ are methyl.

16. The compound of embodiment 1, wherein X is —$NR^7$; Y and Z are O; $R^1$ is methyl; and $R^7$ is H, substituted or unsubstituted alkyl, or substituted or unsubstituted aryl.

17. The compound of embodiment 1, wherein X is —NR$^7$; Y and Z are O; R$^2$ is methyl; and R$^7$ is H, substituted or unsubstituted alkyl, or substituted or unsubstituted aryl.
18. The compound of embodiment 1, wherein X is —NR$^7$; Y and Z are O; R$^3$ is methyl; and R$^7$ is H, substituted or unsubstituted alkyl, or substituted or unsubstituted aryl.
19. The compound of embodiment 1, wherein X is —NR$^7$; Y and Z are O; R$^1$, R$^2$, and R$^3$ are methyl; and R$^7$ is H, substituted or unsubstituted alkyl, or substituted or unsubstituted aryl.
20. The compound of embodiment 1, wherein R$^4$ and R$^5$ together with the carbons to which they are attached form a cycloalkyl, cycloalkenyl, heterocycloalkyl, or heterocycloalkenyl ring, which is optionally substituted with one or more substituents selected from amino, halo, alkyl, cycloalkyl, aryl, and oxo.
21. The compound of embodiment 1, wherein X, Y, and Z are O; R$^3$ is methyl; R$^6$ is —C(O)OR$^8$, —C(S)R$^8$, —C(S)OR$^8$, —C(S)SR$^8$, —C(O)NR$^8$; and R$^8$ is H, or alkyl.
22. The compound of embodiment 1, wherein X is —NR$^7$; Y and Z are O; R$^3$ is methyl; R$^6$ is —C(O)OR$^8$, —C(S)R$^8$, —C(S)OR$^8$, —C(S)SR$^8$, —C(O)NR$^8$; R$^8$ is H or alkyl; and R$^7$ is H, substituted or unsubstituted alkyl, or substituted or unsubstituted aryl.
23. The compound of embodiment 1, wherein X, Y, and Z are O; R$^3$ is methyl; and R$^4$ and R$^5$ together with the carbons to which they are attached form a cycloalkyl, cycloalkenyl, heterocycloalkyl, or heterocycloalkenyl ring, which is optionally substituted with one or more substituents selected from amino, halo, alkyl, cycloalkyl, aryl, and oxo.
24. The compound of embodiment 1, wherein X is —NR$^7$; Y and Z are O; R$^3$ is methyl; and R$^4$ and R$^5$ together with the carbons to which they are attached form a cycloalkyl, cycloalkenyl, heterocycloalkyl, or heterocycloalkenyl ring, which is optionally substituted with one or more substituents selected from amino, halo, alkyl, cycloalkyl, aryl, and oxo; and R$^7$ is H, substituted or unsubstituted alkyl, or substituted or unsubstituted aryl.
25. The compound of embodiment 1, wherein X, Y, and Z are O; R$^3$ is methyl; and R$^4$ and R$^5$ together with the carbons to which they are attached form a cycloalkenyl ring, which is optionally substituted with one or more substituents selected from alkyl, cycloalkyl, aryl, and oxo.
26. The compound of embodiment 1, wherein X is —NR$^7$; Y and Z are O; R$^3$ is methyl; R$^4$ and R$^5$ together with the carbons to which they are attached form a cycloalkenyl ring, which is optionally substituted with one or more substituents selected from amino, halo, alkyl, cycloalkyl, aryl, and oxo; and R$^7$ is H, substituted or unsubstituted alkyl, or substituted or unsubstituted aryl.
27. The compound of embodiment 1, wherein the compound is an isomer.
28. The compound of embodiment 27, wherein the isomer is a geometric isomer.
29. The compound of embodiment 27, wherein the isomer is a stereoisomer.
30. The compound of embodiment 28, which is an E-isomer or a Z-isomer.
31. The compound of embodiment 29, which is an enantiomer and/or a diastereomer.
32. The compound of embodiment 1, which is

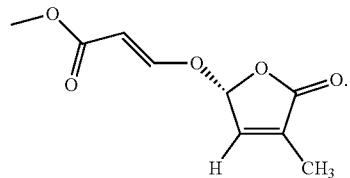

33. The compound of embodiment 1, which is

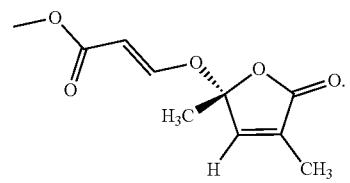

34. The compound of embodiment 1, which is

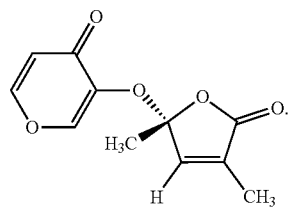 [SMILES: CC1=C[C@](C)(Oc2coccc2=O)OC1=O]

35. The compound of embodiment 1, which is

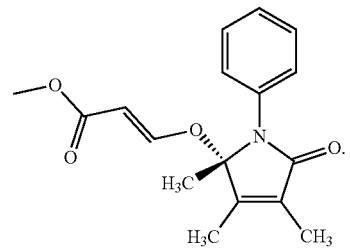 [SMILES: COC(=O)/C=C/O[C@@]1(C)C(C)=C(C)C(=O)N1c1ccccc1]

36. The compound of embodiment 1, which is

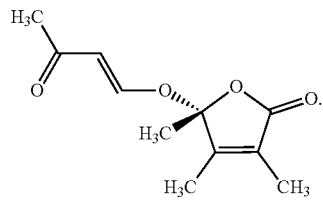

37. The compound of embodiment 1, which is

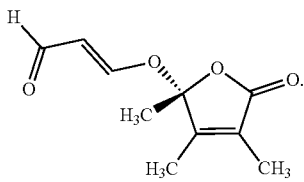

38. A compound of Formula (II):

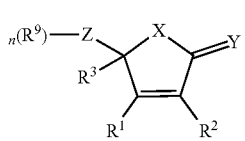

wherein
X, and Y are independently O, S, or —NR$^7$;
Z is O, S, —NH, or A;
R$^1$, R$^2$, and R$^3$ are each independently H, amino, halo, substituted or unsubstituted alkyl, substituted or unsubstituted aryl, substituted or unsubstituted heteroalkyl, substituted or unsubstituted heteroaryl, substituted or unsubstituted arylalkyl, substituted or unsubstituted cycloalkyl, substituted or unsubstituted heterocycloalkyl, —OR$^8$, —SR$^8$, —C(O)R$^8$. —C(O)OR$^8$. —C(S)R$^8$. —C(S)OR$^8$. —C(S)SR$^8$. —C(O)NR$^8$;
R$^7$ and R$^8$ are each independently H, substituted or unsubstituted alkyl, substituted or unsubstituted aryl, substituted or unsubstituted heteroalkyl, substituted or unsubstituted heteroaryl, substituted or unsubstituted arylalkyl, substituted or unsubstituted cycloalkyl, or substituted or unsubstituted heterocycloalkyl;
A is a substituted or unsubstituted heterocyclic group or substituted or unsubstituted heteroaryl group;
R$^9$ is H, substituted or unsubstituted alkyl, substituted or unsubstituted aryl, substituted or unsubstituted heteroalkyl, substituted or unsubstituted heteroaryl, substituted or unsubstituted arylalkyl, substituted or unsubstituted cycloalkyl, substituted or unsubstituted heterocycloalkyl, —C(O)R$^8$, —C(O)OR$^8$, —C(S)R$^8$, —C(S)OR, —C(S)SR, or —C(O)NR$^8$; and
n is 1, 2, or 3;
or a salt or solvate thereof.
39. A formulation comprising:
(i) a compound of Formula (I):

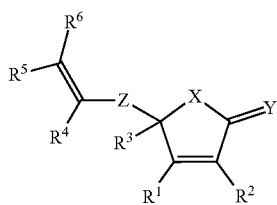

wherein
X, Y, and Z are independently O, S, or —NR$^7$;
R$^1$, R$^2$, R$^3$, R$^4$, R, and R$^6$ are each independently H, amino, halo, substituted or unsubstituted alkyl, substituted or unsubstituted aryl, substituted or unsubstituted heteroalkyl, substituted or unsubstituted heteroaryl, substituted or unsubstituted arylalkyl, substituted or unsubstituted cycloalkyl, substituted or unsubstituted heterocycloalkyl, —OR$^8$, —SR$^8$, —C(O)R$^8$, —C(O) OR$^8$, —C(S)R$^8$, —C(S)OR$^8$, —C(S)SR$^8$, —C(O)NR$^8$;
or R$^4$ and R$^5$ together with the carbons to which they are attached form a cycloalkyl, cycloalkenyl, heterocycloalkyl, or heterocycloalkenyl ring, which is optionally substituted with one or more substituents selected from amino, halo, alkyl, cycloalkyl, aryl, and oxo; and
R$^7$ and R$^8$ are each independently H, substituted or unsubstituted alkyl, substituted or unsubstituted aryl, substituted or unsubstituted heteroalkyl, substituted or unsubstituted heteroaryl, substituted or unsubstituted arylalkyl, substituted or unsubstituted cycloalkyl, or substituted or unsubstituted heterocycloalkyl;
or a salt or solvate thereof; and
(ii) at least one of a plant growth regulator, a fertilizer, an insecticide, an herbicide, a fungicide, a urease inhibitor, a nitrification inhibitor, and an excipient.
40. A formulation comprising:
(i) a compound of Formula (II):

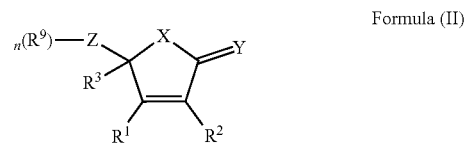

wherein
X and Y are independently O, S, or —NR$^7$;
Z is O, S, —NH, or A;
R$^1$, R$^2$, and R$^3$ are each independently H, amino, halo, substituted or unsubstituted alkyl, substituted or unsubstituted aryl, substituted or unsubstituted heteroalkyl, substituted or unsubstituted heteroaryl, substituted or unsubstituted arylalkyl, substituted or unsubstituted cycloalkyl, substituted or unsubstituted heterocycloalkyl, —OR$^8$, —SR$^8$, —C(O)R$^8$, —C(O)OR$^8$, —C(S)R$^8$, —C(S)OR$^8$, —C(S)SR$^8$, —C(O)NR$^1$;
R$^7$ and R$^8$ are each independently H, substituted or unsubstituted alkyl, substituted or unsubstituted aryl, substituted or unsubstituted heteroalkyl, substituted or unsubstituted heteroaryl, substituted or unsubstituted arylalkyl, substituted or unsubstituted cycloalkyl, or substituted or unsubstituted heterocycloalkyl;
A is a substituted or unsubstituted heterocyclic group or substituted or unsubstituted heteroaryl group;
R$^9$ is H, substituted or unsubstituted alkyl, substituted or unsubstituted aryl, substituted or unsubstituted heteroalkyl, substituted or unsubstituted heteroaryl, substituted or unsubstituted arylalkyl, substituted or unsubstituted cycloalkyl, substituted or unsubstituted heterocycloalkyl, —C(O)R$^8$, —C(O)OR$^8$, —C(S)R$^8$, —C(S)OR$^8$, —C(S)SR$^8$, or —C(O)NR$^8$; and
n is 1, 2, or 3;
or a salt or solvate thereof; and
(ii) at least one of a plant growth regulator, a fertilizer, an insecticide, an herbicide, a fungicide, a urease inhibitor, a nitrification inhibitor, and an excipient.
41. The formulation of embodiment 39 or 40, wherein the compound of Formula (I) or Formula (II) is present in an amount ranging from about 1% to 99% by weight of the total weight of the formulation.

42. The formulation of embodiment 39 or 40, wherein the compound of Formula (I) or Formula (II) is present in an amount of about 1%, 5%, 10%, 20%, 30%, 40%, 50%, 60%, 70%, 80%, 90%, 95%, or 99% by weight of the total weight of the formulation.
43. The formulation of embodiment 39 or 40, wherein the formulation is a powder, a suspension, a gel, or a liquid.
44. The formulation of embodiment 39 or 40, further comprising water, a surfactant, an alcohol, or any combination thereof.
45. The formulation of embodiment 44, wherein the surfactant is selected from sulfosuccinate, naphthalene sulfonate, sulfated ester, phosphate ester, sulfated alcohol, alkyl benzene sulfonate, polycarboxylate, naphthalene sulfonate condensate, phenol sulfonic acid condensate, lignosulfonate, methyl oleyl taurate, and polyvinyl alcohol.
46. The formulation of embodiment 39 or 40, wherein the fertilizer is nitrogen-containing fertilizer, phosphate-containing fertilizer, potassium-containing fertilizer, calcium-containing fertilizer, magnesium-containing fertilizer, sulfur-containing fertilizer, compound fertilizer, and organic fertilizer.
47. The formulation of embodiment 39 or 40, wherein the herbicide is a glyphosate.
48. The formulation of embodiment 47, wherein the glyphosate is N-(phosphonomethyl)glycine.
49. A formulation comprising:
(i) a compound of Formula (I):

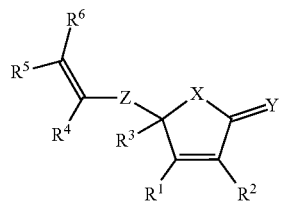

Formula (I)

wherein
X, Y, and Z are independently O, S, or —NR$^7$;
R$^1$, R$^2$, R$^3$, R$^4$, R$^5$, and R$^6$ are each independently H, amino, halo, substituted or unsubstituted alkyl, substituted or unsubstituted aryl, substituted or unsubstituted heteroalkyl, substituted or unsubstituted heteroaryl, substituted or unsubstituted arylalkyl, substituted or unsubstituted cycloalkyl, substituted or unsubstituted heterocycloalkyl, —OR$^8$, —SR$^8$, —C(O)R$^8$, —C(O)OR$^8$, —C(S)R$^8$, —C(S)OR$^8$, —C(S)SR$^8$, —C(O)NR$^8$;
or R$^4$ and R$^5$ together with the carbons to which they are attached form a cycloalkyl, cycloalkenyl, heterocycloalkyl, or heterocycloalkenyl ring, which is optionally substituted with one or more substituents selected from amino, halo, alkyl, cycloalkyl, aryl, and oxo; and
R$^7$ and R$^8$ are each independently H, substituted or unsubstituted alkyl, substituted or unsubstituted aryl, substituted or unsubstituted heteroalkyl, substituted or unsubstituted heteroaryl, substituted or unsubstituted arylalkyl, substituted or unsubstituted cycloalkyl, or substituted or unsubstituted heterocycloalkyl;
or a salt or solvate thereof; and
(ii) a urease inhibitor selected from N—(N-butyl)thiophosphoric triamide (NBPT), N—(N-butyl)phosphoric triamide, thiophosphoryl triamide, phenyl phosphorodiamidate, N-cyclohexyl phosphoric triamide, N-cyclohexyl thiophosphoric triamide, phosphoric triamide, hydroquinone, p-benzoquinone, hexamidocyclotriphosphazene, thiopyridines, thiopyrimidines, thiopyridine-N-oxides, N,N-dihalo-2-imidazolidinone, N-halo-2-oxazolidinone, N-(2-nitrophenyl)thiophosphoric triamide, and N-(2-nitrophenyl)phosphoric triamide.

50. A formulation comprising:
(i) a compound of Formula (I):

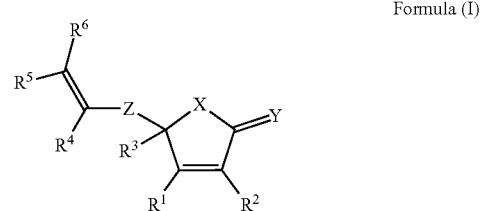

Formula (I)

wherein
X, Y, and Z are independently O, S, or —NR$^7$;
R$^1$, R$^2$, R$^3$, R$^4$, R$^5$, and R$^6$ are each independently H, amino, halo, substituted or unsubstituted alkyl, substituted or unsubstituted aryl, substituted or unsubstituted heteroalkyl, substituted or unsubstituted heteroaryl, substituted or unsubstituted arylalkyl, substituted or unsubstituted cycloalkyl, substituted or unsubstituted heterocycloalkyl, —OR$^8$, —SR$^8$, —C(O)R$^8$, —C(O)OR$^8$, —C(S)R$^8$, —C(S)OR$^8$, —C(S)SR$^8$, —C(O)NR$^8$;
or R$^4$ and R$^5$ together with the carbons to which they are attached form a cycloalkyl, cycloalkenyl, heterocycloalkyl, or heterocycloalkenyl ring, which is optionally substituted with one or more substituents selected from amino, halo, alkyl, cycloalkyl, aryl, and oxo; and
R$^7$ and R$^8$ are each independently H, substituted or unsubstituted alkyl, substituted or unsubstituted aryl, substituted or unsubstituted heteroalkyl, substituted or unsubstituted heteroaryl, substituted or unsubstituted arylalkyl, substituted or unsubstituted cycloalkyl, or substituted or unsubstituted heterocycloalkyl;
or a salt or solvate thereof; and
(ii) a nitrification inhibitor selected from 2-chloro-6-trichloromethyl-pyridine, 5-ethoxy-3-trichloromethyl-1,2,4-thiadiazole, dicyandiamide, 2-amino-4-chloro-6-methyl-pyrimidine, 1,3-benzothiazole-2-thiol, 4-amino-N-1,3-thiazol-2-ylbenzenesulfonamide, thiourea, guanidine, 3,4-dimethylpyrazole phosphate, 2,4-diamino-6-trichloromethyl-5-triazine, polyetherionophores, 4-amino-1,2,4-triazole, 3-mercapto-1,2,4-triazole, potassium azide, carbon bisulfide, sodium trithiocarbonate, ammonium dithiocarbamate, 2,3-dihydro-2,2-dimethyl-7-benzofuranol methyl-carbamate, N-(2,6-dimethylphenyl)-N-(methoxyacetyl)-alanine methyl ester, ammonium thiosulfate, 1-hydroxypyrazole, 2-methylpyrazole-1-carboxamide, and dicyandiamide (DCD).
51. A method of activating the strigolactone-signaling cascade, comprising applying an effective amount of a compound of embodiment 1 to a plant in need thereof.
52. The method of embodiment 51, wherein the compound of Formula (I) binds to the DWARF14 receptor.
53. The method of embodiment 51, wherein the compound of Formula (I) binds to the DWARF14 receptor active site/binding pocket.

54. The method of embodiment 51, wherein the compound of Formula (I) binds to the DWARF14 receptor allosteric site.
55. A method for controlling weeds, comprising applying a seed-germination-promoting amount of a compound of any one of embodiments 1 to 38 to a seed.
56. The method of embodiment 55, wherein the seed germinates.
57. A method for hydraulic enhancement of a plant, comprising contacting a plant with an effective amount of the compound of any one of embodiments 1 to 38.
58. A method for hydraulic enhancement of a plant, comprising contacting a plant with an effective amount of the formulation of embodiment 39 or 40.
59. The method of embodiment 57 or 58, wherein the yield of the contacted plant is increased as compared to a substantially identical but otherwise uncontacted plant.
60. The method of embodiment 57 or 58, wherein transpiration of the contacted plant is increased as compared to a substantially identical but otherwise uncontacted plant.
61. The method of embodiment 57 or 58, wherein the plant is soybean, corn, rice, tomato, alfalfa, wheat, or green algae.
62. The method of embodiment 57 or 58, wherein the plant is corn.
63. The method of embodiment 62, wherein the yield of the contacted corn is increased as compared to a substantially identical but otherwise uncontacted corn.
64. The method of embodiment 63 comprising increasing the yield of the contacted corn, wherein an average kernel mass (w/w) of the contacted corn is increased by at least about 5%, 10%, 15%, 20%, 25%, 30%, 35%, 40%, 45%, 50%, or from about 5% to 50% as compared to a substantially identical but otherwise uncontacted corn.
65. The method of embodiment 63, comprising increasing the yield of the contacted corn, wherein an average ear volume (v/v) of the contacted corn is increased by at least about 5%, 10%, 15%, 20%, 25%, 30%, 35%, 40%, 45%, 50%, or from about 5% to 50% as compared to a substantially identical but otherwise uncontacted corn.
66. The method of embodiment 63, comprising increasing the yield of the contacted corn, wherein an average relative hydration of silks (w/w) of the contacted corn is increased by at least about 5%, 10%, 15%, 20%, 25%, 30%, 35%, 40%, 45%, 50%, or from about 5% to 50% as compared to a substantially identical but otherwise uncontacted corn.
67. The method of embodiment 63, comprising increasing the yield of the contacted corn, wherein an average mass of silks (w/w) of the contacted corn is increased by at least about 5%, 10%, 15%, 20%, 25%, 30%, 35%, 40%, 45%, 50%, or from about 5% to 50% as compared to a substantially identical but otherwise uncontacted corn.
68. A method for increasing transpiration of a plant, comprising contacting a plant with an effective amount of a compound of any one of embodiments 1 to 38, wherein the transpiration of the contacted plant is increased as compared to a substantially identical but otherwise uncontacted plant.
69. The method of embodiment 68, wherein the transpiration of the plant is measured as peak stomatal conductance.
70. The method of embodiment 68, wherein the transpiration of the plant is measured by using a leaf-porometer.
71. The method of embodiment 68, wherein the transpiration of the contacted plant is increased by at least about 5%, 10%, 15%, 20%, 25%, 30%, 35%, 40%, 45%, 50%, or from about 5% to about 50% as compared to a substantially identical but otherwise uncontacted plant.
72. The method of embodiment 68, wherein the transpiration of the plant is measured as transpired water volume.
73. The method of embodiment 72, wherein the transpiration of the plant is measured using an ex vivo hydraulic enhancement assay (xVHS).
74. The method of embodiment 73, wherein the transpiration of the contacted plant is increased by at least about 0.1 mL, 0.2 mL, 0.3 mL, 0.4 mL, 0.5 mL, 0.6 mL, 0.7 mL, 0.8 mL, 0.9 mL, 1.0 mL, or from about 0.1 mL to about 1.0 mL as compared to a substantially identical but otherwise uncontacted plant.
75. The method of embodiment 68, wherein the transpiration of the contacted plant is increased by at least about 5%, 10%, 15%, 20%, 25%, 30%, 35%, 40%, 45%, 50%, or from about 5% to about 50% as compared to a substantially identical but otherwise uncontacted plant.
76. The method of embodiment 57 or 58, wherein the canopy temperature of the plant is lower compared to a substantially identical but otherwise uncontacted plant.
77. The method of embodiment 76, wherein the canopy temperature is measured using an infrared camera.
78. The method of embodiment 76, wherein the canopy temperature of the contacted plant is decreased by at least about 0.1° C., 0.2° C., 0.3° C., 0.4° C., 0.5° C., 0.6° C., 0.7° C., 0.8° C., 0.9° C., 1.0° C., or from about 0.1° C. to about 1.0° C. as compared to a substantially identical but otherwise uncontacted plant.
79. A method of decreasing the permanent wilting point of a plant, comprising contacting a plant with an effective amount of a compound of any one of embodiments 1 to 38.
80. The method of embodiment 79, wherein the permanent wilting point of the contacted plant is decreased as compared to a substantially identical but otherwise uncontacted plant.
81. The method of embodiment 79, wherein the permanent wilting point of the plant is measured as volumetric water content of soil ($m^{33}$).
82. The method of embodiment 81, wherein the permanent wilting point of the contacted plant is decreased by at least about 0.005 $m^3/m^3$, 0.010 $m^3/m^3$, 0.015 $m^3/m^3$, 0.020 $m^3/m^3$, 0.025 $m^3/m^3$, 0.030 $m^3/m^3$, 0.035 $m^3/m^3$, 0.040 $m^3/m^3$, or from about 0.005 $m^3/m^3$ to about 0.040 $m^3/m^3$ as compared to a substantially identical but otherwise uncontacted plant.
83. The method of embodiment 79, wherein the permanent wilting point of the contacted plant is decreased by at least about 5%, 10%, 15%, 20%, 25%, 30%, 35%, 40%, 45%, 50%, or from about 5% to about 50% as compared to a substantially identical but otherwise uncontacted plant.
84. A method for decreasing the cavitation of a plant, comprising contacting a plant with an effective amount of a compound of any one of embodiments 1 to 38, wherein the average rate of cavitation in the xylem of the contacted plant is decreased as compared to a substantially identical but otherwise uncontacted plant.

85. The method of embodiment 84, wherein the average rate of cavitation in the xylem of the plant is measured using an ultrasonic acoustic emission (UAE).

86. The method of embodiment 84, wherein the average rate of cavitation in the xylem of the contacted plant is decreased by at least about 5%, 10%, 15%, 20%, 25%, 30%, 35%, 40%, 45%, 50%, or from about 5% to about 50% as compared to a substantially identical but otherwise uncontacted plant.

87. A method for regulating the growth of a plant, comprising applying a plant-growth-regulating amount of a compound of any one of embodiments 1 to 38 to a plant.

88. A method for promoting the germination of a seed, comprising applying a seed-germination-promoting amount of a compound of any one of embodiments 1 to 38 to a seed.

89. The method of embodiment 57 or 58, wherein the life of the contacted plant is extended as compared to a substantially identical but otherwise uncontacted plant, wilting of the contacted plant is reduced or delayed as compared to a substantially identical but otherwise uncontacted plant, the turgidity of the contacted plant is prolonged or maintained as compared to a substantially identical but otherwise uncontacted plant, the loss of one or more petals of the contacted plant is reduced or delayed as compared to a substantially identical but otherwise uncontacted plant, the chlorophyll content of the contacted plant is maintained as compared to a substantially identical but otherwise uncontacted plant, the loss of the chlorophyll content of the contacted plant is reduced or delayed as compared to a substantially identical but otherwise uncontacted plant, the chlorophyll content of the contacted plant is increased as compared to a substantially identical but otherwise uncontacted plant, the salinity tolerance of the contacted plant is increased as compared to a substantially identical but otherwise uncontacted plant, the water consumption of the contacted plant is reduced as compared to a substantially identical but otherwise uncontacted plant, the drought tolerance of the contacted plant is increased as compared to a substantially identical but otherwise uncontacted plant, pest resistance of the contacted plant is increased as compared to a substantially identical but otherwise uncontacted plant, the pesticide consumption of the contacted plant is reduced as compared to a substantially identical but otherwise uncontacted plant, or any combination thereof.

90. The method of embodiment 87, wherein the plant is subject to an adequately irrigated condition or a drought condition.

91. The method of embodiment 87, wherein the yield of the contacted plant is increased under an adequately irrigated condition or a drought condition.

92. A method for enhancing shoot growth of a plant, comprising contacting the plant with an effective amount of the compound of any one of embodiments 1 to 38, wherein shoot growth is increased as compared to a substantially identical but otherwise uncontacted plant.

93. The method of embodiment 92, wherein the shoot growth is increased by at least about 5%, 10%, 15%, 20%, 25%, 30%, 35%, 40%, 45%, 50%, or from about 5% to about 50% as compared to a substantially identical but otherwise uncontacted plant.

94. The method of embodiment 92, wherein the shoot growth is increased by at least about 50%, 55%, 60%, 65%, 70%, 75%, 80%, 85%, 90%, 95%, 100%, or from about 50% to about 100% as compared to a substantially identical but otherwise uncontacted plant.

95. The method of any one of embodiments 57 to 94, wherein the plant is directly contacted with the compound.

96. The method of embodiment 95, wherein the plant is indirectly contacted by contacting the soil with the compound.

97. The method of embodiment 95, wherein the compound is sprayed on the plant.

98. The method of embodiment 95, wherein the compound is added to an irrigation water of the plant.

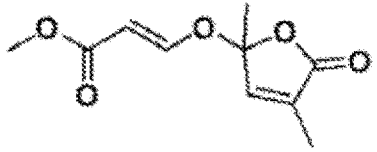

The invention claimed is:

1. A method for hydraulic enhancement of a plant, comprising contacting a plant with
a) an effective amount of a compound of Formula (I):

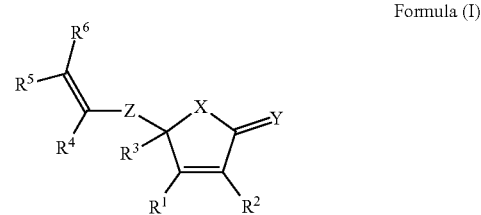

Formula (I)

wherein

X, Y, and Z are independently O, S, or —NR$^7$;

R$_1$, R$^2$, and R$^4$ each independently H, amino, halo, substituted or unsubstituted alkyl, substituted or unsubstituted aryl, substituted or unsubstituted heteroalkyl, substituted or unsubstituted heteroaryl, substituted or unsubstituted arylalkyl, substituted or unsubstituted cycloalkyl, substituted or unsubstituted heterocycloalkyl, —OR$^8$, —SR$^8$, —C(O)R$^8$, —C(O)OR$^8$, —C(S)R$^8$, —C(S)OR$^8$, —C(S)SR$^8$, —C(O)NR$^8$;

R$^3$ is a substituted or unsubstituted alkyl;

R$^5$ is hydrogen;

R$^6$ is —C(O)OR$^8$, —C(S)R$^8$, —C(S)OR$^8$, —C(S)SR$^8$, or —C(O)NR$^8$; and

R$^7$ and R$^8$ are each independently H, substituted or unsubstituted alkyl, substituted or unsubstituted aryl, substituted or unsubstituted heteroalkyl, substituted or unsubstituted heteroaryl, substituted or unsubstituted arylalkyl, substituted or unsubstituted cycloalkyl, or substituted or unsubstituted heterocycloalkyl;

or a salt or solvate thereof; or b) a formulation comprising (i) the compound of Formula (I) or a salt or solvate thereof and (ii) at least one selected from the group of a plant growth regulator, a fertilizer, an insecticide, an herbicide, a fungicide, a urease inhibitor, a nitrification inhibitor, an excipient, and any combination thereof.

2. The method of claim 1, wherein the crop yield of the contacted plant is increased as compared to crop yield of a plant of the same species that is not contacted with the compound of Formula (I).

3. The method of claim 1, wherein transpiration of the contacted plant is increased as compared to transpiration of a plant of the same species that is not contacted with the compound of Formula (I).

4. The method of claim 1, wherein the method comprises contacting the plant with an effective amount of the compound of Formula (I) or a salt or solvate thereof.

5. The method of claim 4, wherein X is O or —$NR^7$; Y and Z are each O; and $R^1$, $R^2$, and $R^4$ are each independently H, substituted or unsubstituted alkyl, or substituted or unsubstituted aryl.

6. The method of claim 4, wherein X is O or —$NR^7$; Y and Z are each O; and $R^1$ and $R^2$ are each independently H, substituted or unsubstituted alkyl, or substituted or unsubstituted aryl.

7. The method of claim 4, wherein X is O or —$NR^7$; Y and Z are each O; $R^1$, $R^2$, and $R^4$ are each independently H or alkyl;
and $R^8$ is H, substituted or unsubstituted alkyl, or substituted or unsubstituted aryl.

8. The method of claim 4, wherein X is O or —$NR^7$; Y and Z are each O; and $R^1$ and $R^2$, are each independently H or alkyl.

9. The method of claim 4, wherein X is O or —$NR^7$; Y and Z are each O; and $R^1$ and/or $R^2$ is methyl.

10. The method of claim 4, wherein X is —$NR^7$; Y and Z are each O; $R^1$ and/or $R^2$ is methyl; and $R^7$ is H, substituted or unsubstituted alkyl, or substituted or unsubstituted aryl.

11. The method of claim 4, wherein X is O or —$NR^7$; Y and Z are each O; and $R^8$ is H or alkyl.

12. The method of claim 4, wherein X is O or —$NR^7$; Y and Z are each O.

13. The method of claim 4, wherein X is O; Y and Z are each O.

14. The method of claim 4, wherein the compound of Formula (I) has a structure of:

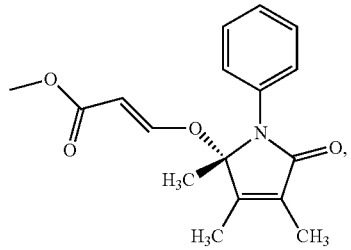

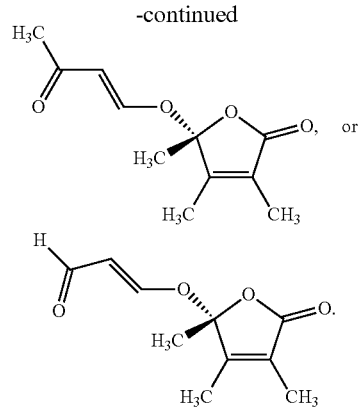

15. The method of claim 1, wherein the method comprises contacting the plant with the formulation comprising (i) the compound of Formula (I) or a salt or solvate thereof; and (ii) at least one selected from the group of a plant growth regulator, a fertilizer, an insecticide, an herbicide, a fungicide, a urease inhibitor, a nitrification inhibitor, an excipient, and any combination thereof.

16. A method for hydraulic enhancement of a plant, comprising contacting a plant with an effective amount of a compound having a structure of:

Formula (I)

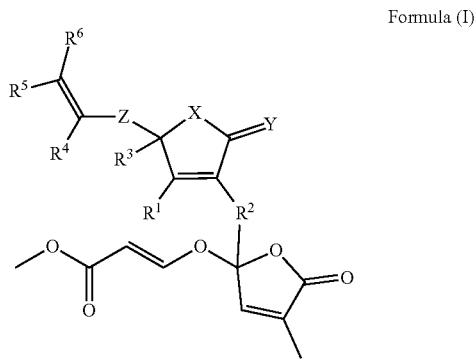

or a salt or solvate thereof.

17. The method of claim 16, wherein the crop yield of the contacted plant is increased as compared to crop yield of a plant of the same species that is not contacted with the compound.

18. The method of claim 16, wherein transpiration of the contacted plant is increased as compared to transpiration of a plant of the same species that is not contacted with the compound.

* * * * *

UNITED STATES PATENT AND TRADEMARK OFFICE
CERTIFICATE OF CORRECTION

PATENT NO. : 11,787,763 B2
APPLICATION NO. : 16/764444
DATED : October 17, 2023
INVENTOR(S) : Adnani et al.

It is certified that error appears in the above-identified patent and that said Letters Patent is hereby corrected as shown below:

On the Title Page

Item (54) Title: Please correct "DERIVAUVES" to read --DERIVATIVES--

In the Specification

Column 1, Line 1: Please correct "DERIVAUVES" to read --DERIVATIVES--

Column 5, Line 5: Please correct "—C(O)NRs" to read -- —C(O)NR$^8$--

Column 6, Lines 17-27, Formula (D): Please remove the formula and replace with the following:

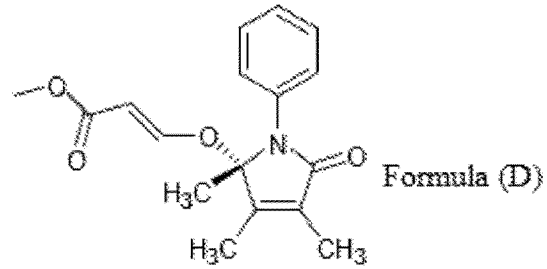

Column 9, Line 21: Please correct "—OR, —SR," to read -- —OR$^8$, —SR$^8$,--

Column 10, Line 48: Please correct "(NH$_4$)" to read --(NH$_4^+$)--

Column 10, Line 50: Please correct "(NH$_4$)" to read --(NH$_4^+$)--

Column 24, Line 2: Please correct "Professional@" to read --Professional®--

Column 26, Line 32: Please correct "R, R$^2$," to read --R$^1$, R$^2$,--

Signed and Sealed this
Twentieth Day of February, 2024

*Katherine Kelly Vidal*

Katherine Kelly Vidal
*Director of the United States Patent and Trademark Office*

Column 29, Line 47: Please correct "—C(S)OR, —C(S)SR," to read -- —C(S)OR$^8$, —C(S)SR$^8$,--

Column 29, Line 66: Please correct "R$^4$, R," to read --R$^4$, R$^5$,--

Column 30, Line 43: Please correct "—C(O)NR$^1$" to read -- —C(O)NR$^8$--

Column 34, Line 50: Please correct "(m$^{33}$)" to read --(m$^3$/m$^3$)--

In the Claims

Column 36, Line 38, Claim 1: Please correct "R$_1$" to read --R$^1$--

Column 38, Lines 30-44, Formula (1), Claim 16: Please remove the formula and replace with the following: